(12) United States Patent
Wernet

(10) Patent No.: US 7,556,801 B2
(45) Date of Patent: Jul. 7, 2009

(54) HUMAN CORD BLOOD DERIVED UNRESTRICTED SOMATIC STEM CELLS (USSC)

(75) Inventor: Peter Wernet, Dusseldorf (DE)

(73) Assignee: Kourion Therapeutics GmbH, Dusseldorf (DE)

( * ) Notice: Subject to any disclaimer, the term of this patent is extended or adjusted under 35 U.S.C. 154(b) by 570 days.

(21) Appl. No.: 10/758,644

(22) Filed: Jan. 15, 2004

(65) Prior Publication Data

US 2005/0142118 A1 Jun. 30, 2005

(51) Int. Cl.
*A01N 63/00* (2006.01)
*C12N 5/00* (2006.01)

(52) U.S. Cl. .................... 424/93.1; 435/372
(58) Field of Classification Search ............... None
See application file for complete search history.

(56) References Cited

U.S. PATENT DOCUMENTS

| | | | |
|---|---|---|---|
| 5,057,426 A | 10/1991 | Henco et al. | |
| 5,486,359 A | 1/1996 | Caplan et al. | |
| 5,672,346 A | 9/1997 | Srour et al. | |
| 5,842,477 A * | 12/1998 | Naughton et al. | 128/898 |
| 5,843,633 A | 12/1998 | Yin et al. | |
| 5,851,832 A | 12/1998 | Weiss et al. | |
| 6,387,369 B1 * | 5/2002 | Pittenger et al. | 424/93.7 |
| 6,482,231 B1 * | 11/2002 | Abatangelo et al. | 623/11.11 |
| 2004/0197310 A1 * | 10/2004 | Sanberg et al. | 424/93.7 |
| 2005/0118714 A1 * | 6/2005 | Ha et al. | 435/372 |

FOREIGN PATENT DOCUMENTS

| | | |
|---|---|---|
| JP | 63 150294 | 6/1988 |
| JP | 10-295369 | 11/1998 |
| JP | 10-306027 | 11/1998 |
| WO | WO 97/39104 | * 10/1997 |
| WO | WO 99/03973 | * 1/1999 |
| WO | WO 00/06705 | 2/2000 |
| WO | WO 00/64459 | 11/2000 |

OTHER PUBLICATIONS

Andrea-Romana et al. Oct-4-expressing cells in human amniotic fluid: a new source of stem cell research? Human Reproduction 18:1489-1493, 2003.*
Park et al. Global gene and cell replacement strategies via stem cells. Gene therapy 9:613-624, 2002.*
Kaufman et al. Hematopoietic colony-forming cells derived from human embryonic stem cells. PNAS 98:10716-10721, 2001.*
Grounds et al. The role of stem cells in skeletal and cardiac muscle repair. J. Histochem. Cytochem. 50:589-610, 2002.*
Alfonso et al., "Osteoblast precursor cells are found in the low-density fraction of umbilical cord blood," 94(10:Suppl.1):161 (b), *Forty-first Annual Meeting of American Society of Hematology*, New Orleans, LA (1999).
Arnold, "Mesenchymal stem cells," *J. Ortho. Res.* 9:641-650 (1991).
Bruder et al., Mesenchymal stem cells in bone development, bone repair, and skeletal regeneration therapy, *J. Cell. Biochem.* 56:283-294 (1994).
Erices et al., "Mesenchymal progenitor cells in human umbilical cord blood," *British Journal of Hematology* 109:235-242 (2000).
Gutierrez-Rodriguez et al., "Characterization of the adherent cells developed in Dexter-type long-term cultures from human umbilical cord blood," *Stem Cells* 18:46-52 (2000).
Goodwin et al., "Multineage differentiation activity by cells isolated from umbilical cord blood: expression of bone, fat, and neural markers," *Biology of Blood and Marrow Transplantation* 7:581-588 (2001).
Hagiwara et al., ISBN 4-06 129832-1 (KS), NDC 579 (with English translation) p. 22 (1974).
Hall et al., "Overexpression of the hyaluronan receptor RHAMM is transforming and is also required for H-ras transformation," *Cell* 82:19-28 (1995).
Holden et al., "Plasticity: time for a reappraisal," *Science* 296:2126-2129 (2002).
Itano et al., "Expression cloning and molecular characterization of HAS protein, a eukaryotic hyaluronan synthase," *J. Biol. Chem.* 271:9875-9878 (1996).
Jaiswal et al., "Osteogenic differentiation of purified, cultured-expanded human mesenchymal stem cells in vitro," *J. Cell. Biochem.* 64:295-312 (1997).
Johnstone et al., "In vitro chondrogenesis of bone marrow-derived mesenchymal progenitor cells," *Exp. Cell Res.* 238:265-272 (1998).
Knittel et al., "Localization of liver myofibroblasts and hepatic stellate cells in normal and diseased rat livers: distinct role of (myo-)fibroblast subpopulations in hepatic tissue repair," *Histochem. Cell Biol.* 112:387-401 (1999).
Maresch et al., "Haematologica 2001," *Scientific Correspondence* 86:1099-1100 (2001).
Ramirez-Zacarias et al., "Quantitation of adipose conversion and triglycerides by staining intracytoplasmic lipids with oil red O," *Histochem.* 97:493-497 (1992).
Rosenbaum et al., "Isolation and characterization of schwann cells from neurofibromatosis type 2 patients," *Neurobiol. Dis.* 5:55-64 (1998).
Rungby et al., "The von Kossa reaction for calcium deposits: silver lactate staining increases sensitivity and reduces background," *Histochem.* 25:446-451 (1993).
Sanchez-Ramos et al., "Expression of neural markets in human umbilical cord blood," *Exp. Neurol.* 171:109-115 (2001).

(Continued)

*Primary Examiner*—Quang Nguyen
(74) *Attorney, Agent, or Firm*—Clark & Elbing LLP

(57) ABSTRACT

A composition in human cord and placental blood which comprises unrestricted somatic stem cells is described here which can be amplified in vitro to large quantities sufficient for medical applications as regenerative medicines. Initiation and maintenance as well as ex vivo expansion protocols of such stem cells from cord blood is described.

Furthermore, it is shown that from these cells employing varying differentiation induction protocols distinct lineage progenitors for hematopoiesis and endothel, as well as mesenchymal progenitors for muscle bone, cartilage and fat as well as neural progenitors can be cultured and expanded for use in regenerative medicine.

1 Claim, 19 Drawing Sheets

OTHER PUBLICATIONS

Shapiro et al., "Islet transplantation in seven patients with type 1 diabetes mellitus using a glucocoriticoid-free immunosuppressive regimen," *NEJM* 343:230-238 (2000).

Sirchia et al., "Placenta/umbilical cord blood transplantation," *Haematologica* 84:738-747 (1999).

Stanford et al., "Rapidly forming apatitic mineral in an osteoblastic cell line (UMR 106-01 BSP)," *J. Biol. Chem.*, 270:9420-9428 (1995).

Sztrolovics et al, "Localization of the human fibromodulin gene (FMOD) to chromosome 1q32 completion of the cDNA sequence," *Genomics* 23:715-717 (1994).

Takahatu, "Adsorption chromatography of nucleic acids on silicone-coated porous glass," *J. Biochem.* 94:163-169 (1983).

Te-Cheng Pan et al., "Structure and expression of fibulin-2, a novel extracellular matrix protein with multiple EGF-like repeats and consensus motifs for calcium binding," *J. Cell Biol.* 123:1269-1277 (1993).

Tsuda et al., "Fibulin-2 expression marks transformed mesenchymal cells in developing cardiac valves, aortic arch vessels, and coronary vessels," *Developmental Dynamics* 222:89-100 (2001).

Verfaillie et al., "Stem cells: hype and reality," *Hematol.* (Am. Soc. Hematol. Educ. Program) 369-391 (2002).

Vogel et al., "Studies cast doubt on plasticity of adult cells," *Science* 295:1989-1991 (2002).

Wernel et al., "Detection of unrestricted multipotential stem cells in human cord blood," *Blood* 98:550a (2001).

Yoo et al., "The chonddrogenic potential of human bone-marrow derived mesenchymal progenitor cells," *J. Bone Joint Surgery* 80-A:1745-1757 (1998).

Zhang et al., "Fibulin-2 (FBLN2): human cDNA sequence, mRNA expression, and mapping of the gene on human and mouse chromosomes," *Genomics* 22:425-430 (1994).

Bjorklund and Svendsen, "Breaking the Blood Barrier," *Nature* 397:569-570 (1999).

Goodison et al., "CD44 Cell Adhesion Molecules," *J. Clin. Pathol. Mol. Pathol.* 52: 189-196, 1999.

Ferrari et al., "Muscle Regeneration by Bone Marrow-Derived Myogenic Progenitors," *Science* 279:1528-1530, 1998.

Prockop, "Marrow Stromal Cells as Stem Cells for Nonhematopoietic Tissues," *Science* 276:71-74, 1997.

Silva et al., "The Profile of Gene Expression of Human Marrow Mesenchymal Stem Cells," *Stem Cells* 21:661-669, 2003.

Ye et al., "Establishment of an Adherent Cell Feeder Layer From Human Umbilical Cord Blood for Support of Long-Term Hematopoietic Progenitor Cell Growth," *Cell Biology* 91:12140-12144, 1994.

* cited by examiner

Figure 2

Gene-Chip Data on USSC Cardiac-Related Genes

| Gene Name | USSC - P2 | Unigene Description |
|---|---|---|
| *Cardiac* | | |
| ATP2A2 | ++++ | ATPase, Ca++ transporting, cardiac muscle, slow twitch 2 |
| ATP2A2 | ++++ | ATPase, Ca++ transporting, cardiac muscle, slow twitch 2 |
| ATP5A1 | +++++ | ATP synthase, H+ transporting, mitochondrial F1 complex, alpha subunit, isoform 1, cardiac muscle |
| CARP | + | cardiac ankyrin repeat protein |
| CASQ2 | - | calsequestrin 2 (cardiac muscle) |
| CDH5 | + | cadherin 5, type 2, VE-cadherin (vascular epithelium) |
| CSRP3 | + | cysteine and glycine-rich protein 3 (cardiac LIM protein) |
| CSX | - | cardiac-specific homeo box |
| DES | - | Human Desmin gene |
| GATA4 | - | GATA-binding protein 4 |
| GJA1 | ++++ | cardiac gap junction protein, alpha 1, 43kD (connexin 43) |
| KCNQ1 | ++ | kidney and cardiac potassium voltage-gated channel, KQT-like subfamily, member 1 |
| MEF2C | ++ | MADS box transcription enhancer factor 2, polypeptide C (myocyte enhancer factor 2C) |
| MEF2C | ++ | MADS box transcription enhancer factor 2, polypeptide C (myocyte enhancer factor 2C) |
| MEF2D | +++ | MADS box transcription enhancer factor 2, polypeptide D (myocyte enhancer factor 2D) |
| MYH6 | + | myosin, heavy polypeptide 6, cardiac muscle, alpha (cardiomyopathy, hypertrophic 1) |
| MYH7 | - | myosin, heavy polypeptide 7, cardiac muscle, beta |
| MYL2 | ++ | myosin, light polypeptide 2, regulatory, cardiac, slow |
| NPPA | + | natriuretic peptide precursor A, cardiac atrium and ventricle |
| TNNC1 | + | troponin C, slow twitch skeletal/cardiac |
| TNNT2 | - | troponin T2, cardiac |

A
B
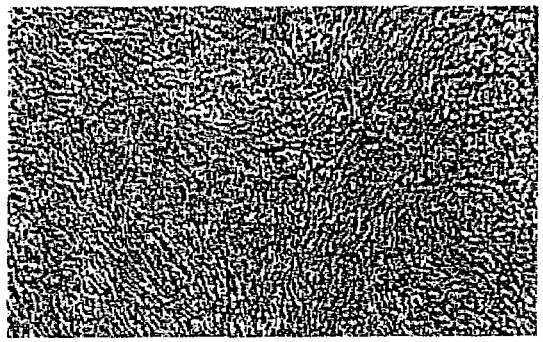
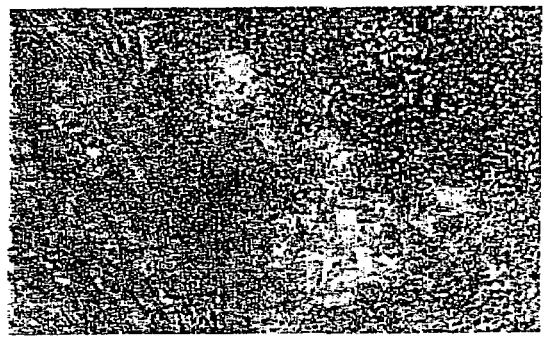
Fig. 12

A
B
Fig. 13

Before Induction                After Induction (1 week)
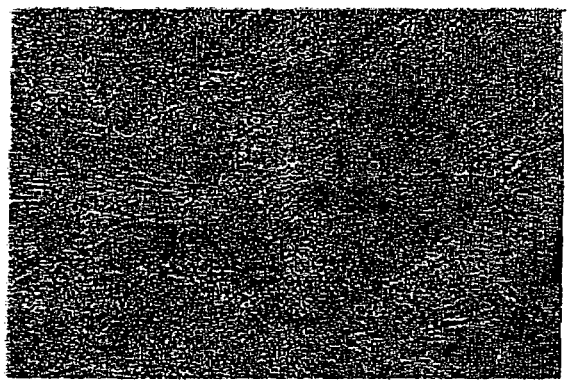 
Fig. 15

Before Induction
After Induction
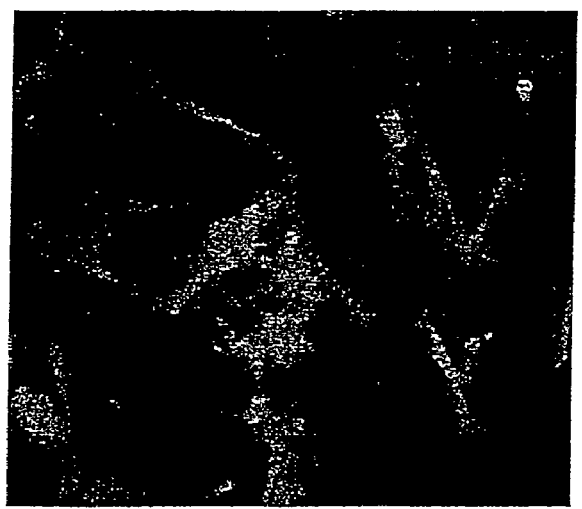
Green: slow Myosin; Red CD13
Fig. 16

HUMAN CORD BLOOD DERIVED UNRESTRICTED SOMATIC STEM CELLS (USSC)

This is a complete application claiming benefit of provisional 60/245,168 filed Nov. 3, 2000.

The present invention pertains to a somatic stem cell, a plurality of stem cells, a medicament comprising the stem cell of the invention and a method for purification, isolation and unique differentiation-potential of the stem cell of the invention.

Although stem cells are permanently self-replacing, they are generally slow cycling. Conventionally, it is thought that these cells give rise to a transient amplifying cell population with limited self-renewal capacity to increase numbers of differentiated cells. Hitherto, the challenge has been to locate stem cells in the adult human and, therefore, a number of surrogate markers (e.g. colony forming tests for the hematopoietic lineage) have been employed in the existing literature.

A number of US-Patents e.g. U.S. Pat. Nos. 5,486,359; 5,591,625; 5,736,396; 5,811,094; 5,827,740; 5,837,539; 5,908,782; 5,908,784; 5,942,225; 5,965,436; 6,010,696; 6,022,540; 6,087,113; 5,858,390; 5,804,446; 5,846,796; 5,654,186; 6,054,121; 5,827,735; 5,906,934 are dealing with mesenchymal stem cells (MSC), which can be differentiated into several progenitor cells, for example muscle progenitor cells, connective tissue cell progenitors or oval cells. Muscle progenitor cells are differentiating further into cardiac, skeletal as well as smooth muscle cells, whereas the connective tissue cell progenitor may differentiate into bone, cartilage as well as fat. Oval cells can differentiate into liver or pancreas cells (Grompe et al, 2001).

The presence of non-hematopoietic stem cells within umbilical cord blood is still under discussion (Mayani et al. 2000, Mareschi et al. 2001). The German patent application DE 198 03 267 A1 was the first to describe osteoblast progenitors and bone formation from human cord blood.

However, the use of these mesenchymal progenitor cells of prior art is often limited since they are too far developed in order to be useful tools for generating organs or tissues. In other words, they seem to be already too much committed and specialized to yield a functional regenerating organ or tissue.

It is therefore an object of the invention to provide a stem cell which is able to differentiate into different progenitor cells such as mesenchymal cells, neural cells, blood cells or endothelial cells.

It is another object of the invention to provide a stem cell which does not have the drawbacks of embryonic stem cells.

It has been found that a newly identified somatic stem cell is able to solve the objects addressed above. The somatic stem cell of the invention is derived from human umbilical cord blood, placental blood and/or the blood from a newborn child, said somatic stem cell being distinct from but capable to differentiate into mesenchymal stem or progenitor cells, hematopoietic lineage stem or progenitor cells, neural stem or progenitor cells or endothelial stem or liver progenitor cells. These cells represent the progenitor of the hematopoietic lineage, the mesenchymal stem cells as well as neural stem cells. This unique multifunctional capacity and the technology to expand these cord blood (CB) derived unrestricted somatic stem cells (USSC), either as such somatic stem cells or as committed cells under distinct differentiation protocols, allows precise characterization, standardization and utilization for the production and implementation of stem cell therapy in regenerative medicine.

FIG. 2 shows a photomicrograph of confluent USSC culture.

FIG. 12 shows Alcian Blue staining of USSC-derived pellet culture.

FIG. 13 shows collagen type II staining (green) of USSC cultures after chondrogenic differentiation.

FIG. 15 shows photomicrographs of USSC cultures before and after myogenic differentiation.

FIG. 16 shows immunocytochemistry for slow-acting myosin after azacytidine treatment.

Figure 1:
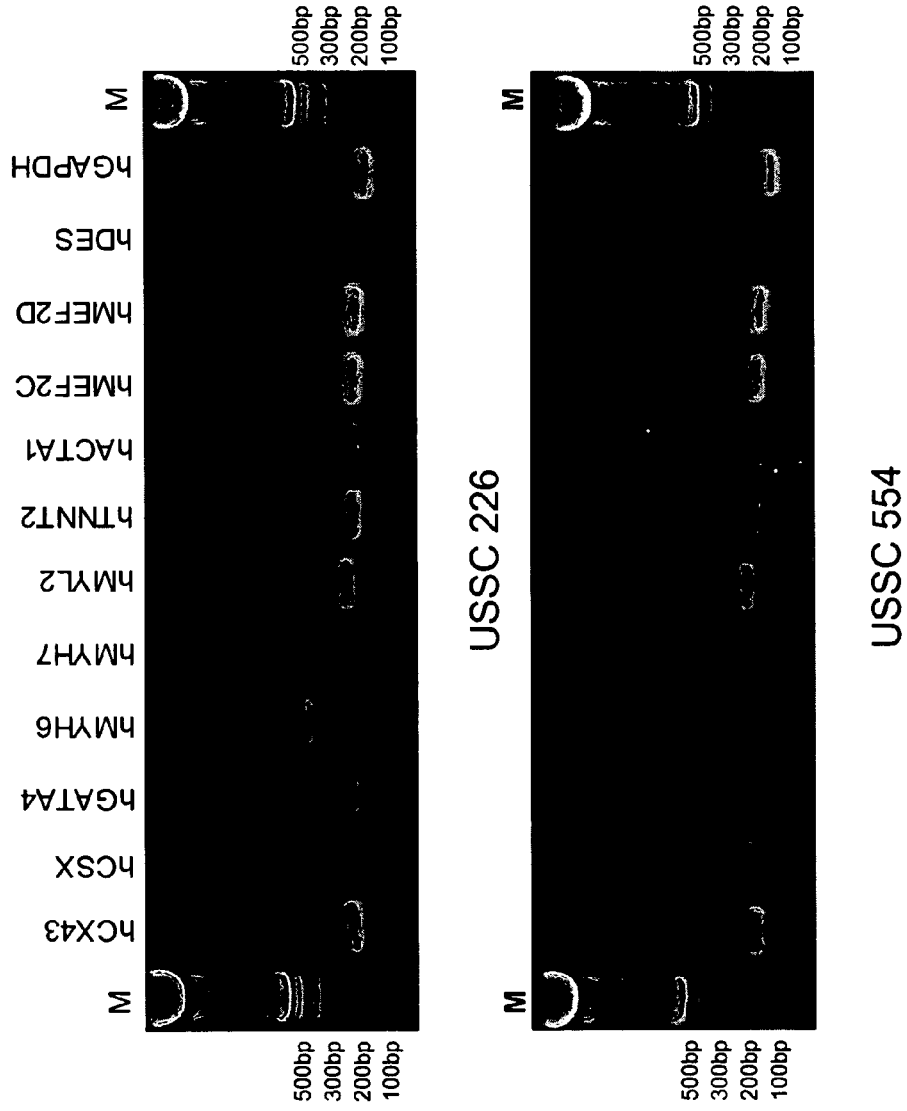
FIG. 1 shows a photomicrograph of primary USSC culture Cells plated at low density.

The somatic stem cells of the invention can be isolated and purified by several methods comprising the steps of density gradient isolation, culture of adherent cells and subculture applying growth factors as described in example 1. After a confluent cell layer has been established, the isolation process to derive cells of this invention is routinely controlled by morphology (fibroblastoid morphology) and phenotypical analyses using antibodies directed against CD13 (positive), CD14 (negative), CD45 (negative), and CD29 (positive; see example 2) surface antigens.

The somatic stem cell of the invention is reacting negatively with markers specific for the hematopoietic lineage such as CD45 and hence, is distinct from hematopoietic stem cells which can also be isolated from placental cord blood. CD14 is another surface antigen that can not be detected on USSCs. Further, the stem cell of this invention is characterized by a set of antigens which are present on the cell surface such as CD13, CD29, CD44, and CD49e. USSC preparations are further characterized by the presence of mRNA transcripts for certain receptor molecules like epidermal growth factor receptor (EGF-R), platelet derived growth factor receptor alpha (PDGF-RA), and insulin growth factor receptor (IGF-R). These cells are also typically expressing transcription factors such as YB1 (Y-box transcription factor 1), Runx1 (runt related transcription factor 1) and AML1C (acute myeloid leukemia 1 transcription factor) as detected by RT-PCR. However, USSC preparations are typically negative for transcripts for the chondrogenic transcription factor Cart-1 and neural markers such as neurofilament, synaptophysin, tyrosine hydroxylase (TH) and glial fibrillary acidic protein (GFAP).

TABLE 1

Analysis of the transcription patterns of USSCs by RT-PCR RT-PCR results achieved with predicted oligonucleotide primers and mRNAs from USSCs and positive control mRNAs from other tissues like bone, cartilage, brain or cord blood mononuclear cells.

| Name | PCR-result USSC | PCR-result (other tissue) |
|---|---|---|
| PDGFR alpha | + | + (adult bone) |
| IGFR | + | + (adult bone) |
| Neurofilament | − | + (adult liver) |
| CD105 | + | + (mononuclear cells from CB) |
| GFAP | − | + (fetal brain) |
| Synaptophysin | − | + (fetal brain) |
| Tyrosinhydroxylase | − | + (fetal brain) |
| YB1 | + | + (fetal brain) |
| Runx1 | + | + (adult bone) |
| AML1c | + | + (adult bone) |
| BMPR II | + | + (adult cartilage) |
| Collagen type I | + | + (adult bone) |
| Cart-1 | − | + (mononuclear cells from CB) |
| Chondroadherin | − | + (adult bone) |
| CD49e | + | + (adult bone) |

The RNA expression of USSC preparations and bone marrow derived MSCs (Caplan, 1991) were directly compared by using quantitative Affymetrix GeneChip™ microarrays. The transcript of the Fibulin-2 gene (gene bank number X82494) was detected in USSCs at high expression levels but not in MSCs. Fibulin-2 production was previously demonstrated in fibroblasts (Pan et al., 1993). Northern blot analysis of mRNA from various human tissues reveals an abundant 4.5-kb transcript in heart, placenta and ovary tissues (Zhang et al., 1994). The protein has been localized at the light microscopical level in human embryos of gestational weeks 4-10, using polyclonal antibodies. Fibulin-2 was detected primarily within the neuropithelium, spinal ganglia and peripheral nerves (Miosge et al., 1996)

In the rat animal model, rat liver myofibroblasts (rMF) are colocalized with fibulin-2. These cells were located in the portal field, the walls of central veins, and only occasionally in the parenchyma. In early stages of fibrosis rMF were detected within the developing scars. In advanced stages of fibrosis rMF accounted for the majority of the cells located within the scar (Knittel et al., 1999). In an other animal model, mouse Fibulin-2 protein is expressed during epithelial-mesenchymal transformation in the endocardial cushion matrix during embryonic heart development. Fibulin-2 is also synthesized by the smooth muscle precursor cells of developing aortic arch vessels and the coronary endothelial cells that are originated from neural crest cells and epicardial cells, respectively (Tsuda et al., 2001).

The transcripts of the Hyaluronan Synthase gene (D84424), Fibromodulin gene (U05291) and the transcript 1NFLS (W03846) were not detected in USSCs but at high levels in MSCs. Northern blot analysis indicated that the Hyaluronan Synthase is ubiquitously expressed in human tissues (Itano and Kimata, 1996). The product of this enzyme, Hyaluronan, serves a variety of functions, including space filling, lubrication of joints, and provision of a matrix through which cells can migrate (Hall et al., 1995). Fibromodulin is a member of a family of small interstitial proteoglycans. The protein exhibits a wide tissue distribution, with the highest abundance observed in articular cartilage, tendon, and ligament (Sztrolovics et al., 1994). The transcript 1NFLS was cloned from human fetal liver.

The CD24 gene (L33930) is expressed in a very low level in the USSCs compared with the expression level in the MSCs. CD24 is expressed in many B-lineage cells and on mature granulocytes (Van der Schoot et al., 1989).

When compared to MSCs, the somatic cells of this invention are distinct based on the tissue source they are isolated from. Further, USSCs are characterized by no expression of human leukocyte antigen class I (HLA-class I). In contrast to the somatic stem cells of this invention, the previously described MSCs isolated from bone marrow and muscle tissue, express very high levels of HLA-class I antigen on their cell surface. The cell of this invention also expresses the stage specific early antigen 4 (SSEA4) (see FIG. 4).

Typically, the somatic stem cell of the invention shows fibroblastoid cell shape and proliferates in an adherent manner.

In a preferred embodiment of the present invention the somatic stem cell of the invention (USSC) is present in a plurality or mixtures representing precursors of other somatic stem cells e.g. of the haematopoietic lineage preferably expressing AC133 and CD34, mesenchymal progenitor somatic stem cells, neuronal progenitor somatic stem cells or combinations thereof. This embodiment is advantageous since it comprises a high regenerative potential based on the capability to differentiate into other different somatic stem cells or the presence of such somatic stem cells as preferred embodiment of the invention. Preferably the mesenchymal progenitor somatic stem cells or the neural progenitor somatic stem cells are produced by differentiation from a stem cell of the invention.

According to the invention a medicament (regenerative therapeutic) is provided comprising the somatic stem cells of the invention as well as a plurality or mixtures of somatic stem cells according to the invention. The medicament may further contain carrier substances or auxiliary substances, which are medically and pharmacologically acceptable. The present invention is also related with a method of using USSC or a plurality or mixtures of stem cells of the invention in gene therapy, organ replacement, testing of pharmaceuticals, in vitro growth of blood vessels, therapy of vascular, bone, hepatic, pancreatic and neural diseases.

For example, the USSCs of the present invention may be applied locally at the site of need, e.g. with or without biomaterials.

Depending on the kind of disease local and/or systemic administration of the USSCs is suitable. The USSCs may be applied directly or together with pharmaceutically acceptable carriers or adjuvants. It may be advantageous to add further substances which promote curing of the diseases. For example, in orthopedic applications substances which improve bone regeneration may be co-applied with the USSCs.

Basically, the methods known for the application of MSCs can be applied in an analogous manner when applying USSCs. Furthermore, the application of stem cells is described for example in B. E. Strauer et al. M. "Intrakoronare, humane autologe Stammzelltransplantation zur Myokardregeneration nach Herzinfarkt", Dtsch med Wochenschr 2001; 126: 932-938; Quarto R., et al. "Repair of Large Bone Defects with the Use of Autologous Bone Marrow Stromal Cells", N Engl J Med 2001; 344:385-386; Vacanti C. A., "Brief Report:Replacement of an Avulsed Phalanx with Tissue-Engineered Bone" N Engl J Med 2001; 344:1511-1514, May 17, 2001; Hentz V. R., "Tissue Engineering for Reconstruction of the Thumb", N Engl J Med 2001; 344:1547-1548; Brittberg M., "Treatment of Deep Cartilage Defects in the Knee with Autologous Chondrocyte Transplantation", N Engl J Med 1994; 331:889-895, Oct. 6, 1994; Freed C. R., "Transplantation of Embryonic Dopamine Neurons for Severe Parkinson's Disease",N Engl J Med 2001; 344:710-719; Shin'oka T., "Transplantation of a Tissue-Engineered Pulmonary Artery", N Engl J Med 2001; 344:532-533. Shapiro A. M. J., Islet Transplantation in Seven Patients with Type 1 Diabetes Mellitus Using a Glucocorticoid-Free Immunosuppressive Regimen N Engl J Med 2000; 343:230-238. These references are incorporated by reference.

The stem cells of the invention are further described in greater detail.

The stem cells of the invention are adherent cells with a fibroblastoid cell shape and two or three nucleoli (see FIG. 1) obtained after trypsin EDTA-treatment and reseeding under appropriate culture conditions (example 1) rapidly expand to confluence of a long stretched morphology (FIG. 2). FIG. 1 shows a photomicrograph of primary USSC culture. The cells plated at low density demonstrate the fibroblastoid morphology of USSCs. These cells can readily be grown over greater than 14 culture passages. FIG. 2 shows a photomicrograph of confluent USSC culture. Almost confluent cell USSC layer shows a parallel orientation of cells.

Figure 3:
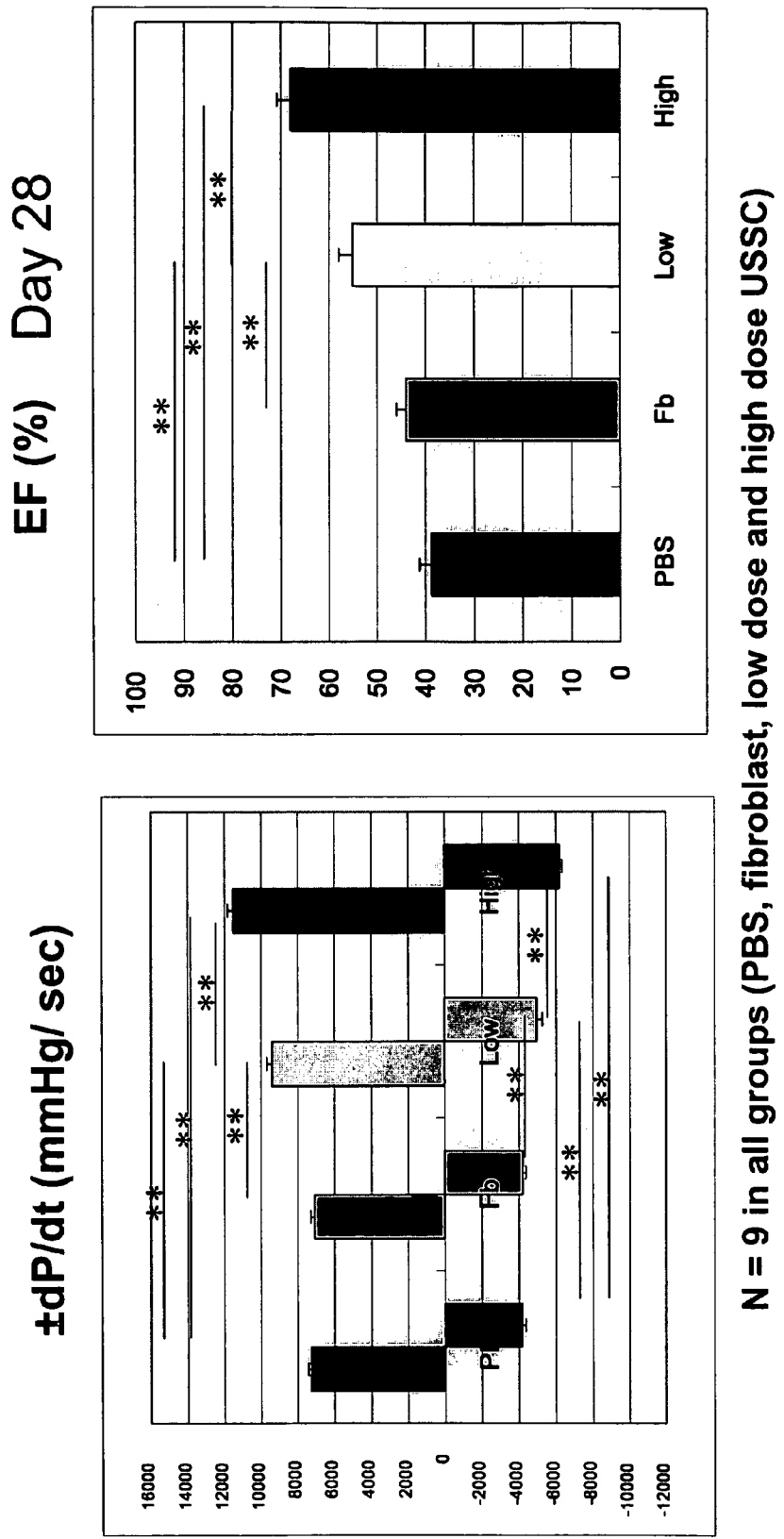
FIG. 3 shows a FACS analysis for CD45 antigen over course of in vitro culture.
Figure 4:
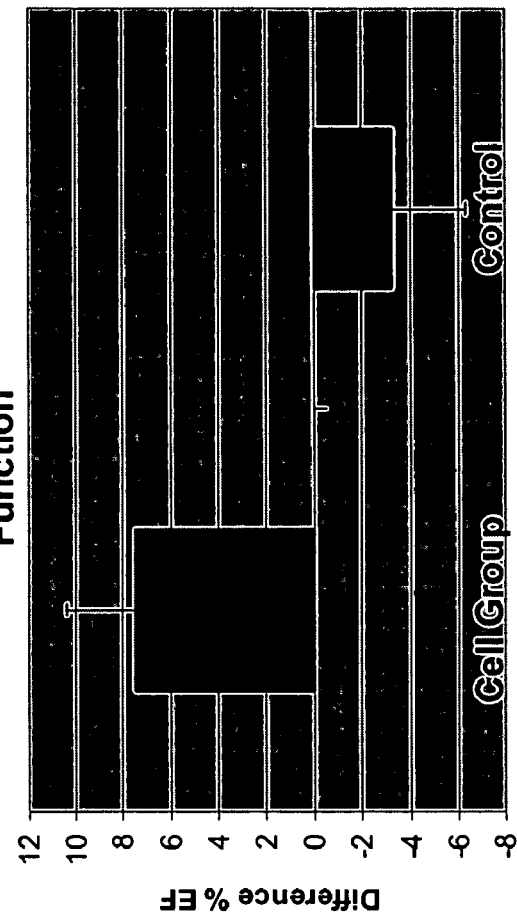
FIG. 4 shows a FACS analysis for SSEA4 embryonic marker.
Figure 5:
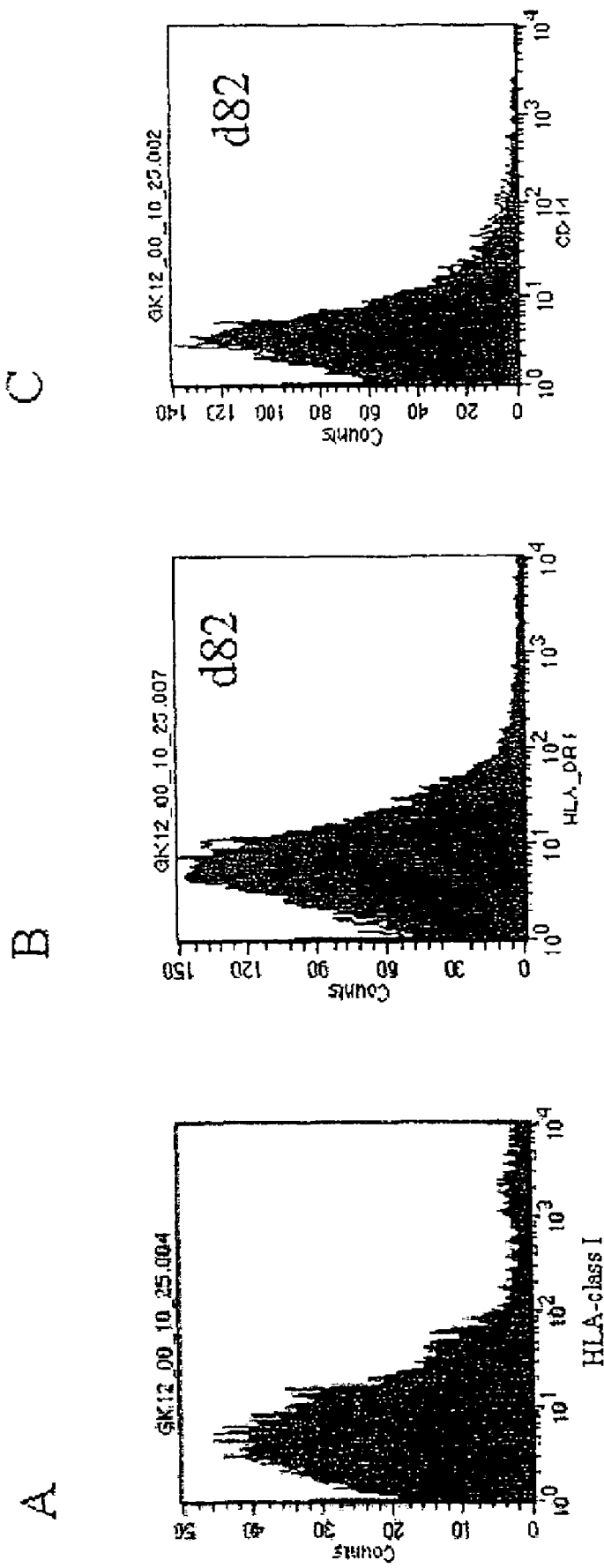
FIG. 5 shows a FACS analysis for HLA-class I (A,B,C), HLA DR and CD14.

The surface marker phenotype of the primary adherent cell layer as well as all derivatives thereof in subsequent passages are and remain negative for the CD45 marker. FIG. 3 shows a FACS analysis for CD45 antigen over the course of in vitro culture. CD45, a characteristic marker antigen for hematopoietic cell is almost not detectable in USSCs from later passages. (FIG. 3 at days 48, 54, 82). After in vitro culture using method A (example 1), USSC preparations become positive for the stage-specific early antigen 4 (SSEA4) and show the homogenous expression of this embryonic marker. FIG. 4 shows a FACS analysis for SSEA4 embryonic marker. Cells expanded by method A (example 1) strongly show expression of the stage-specific early antigen 4 (SSEA4). At the same time, USSC cultures are negative for HLA-class I surface antigen expression. (FIG. 5A), HLA-DR antigen expression (FIG. 5B) as well as CD14 negative (FIG. 5C). FIG. 5 shows a FACS analysis for HLA-class I (A,B,C), HLA DR and CD14. USSC cultures of the invention after expansion in vitro are negative for HLA-class I antigens (Panel A). These cells are also negative for HLA-DR (Panel B) and CD14 (Panel C) surface antigens, characteristic for antigen presenting cells (HLA-DR) and monocytes (CD14).

Figure 6:
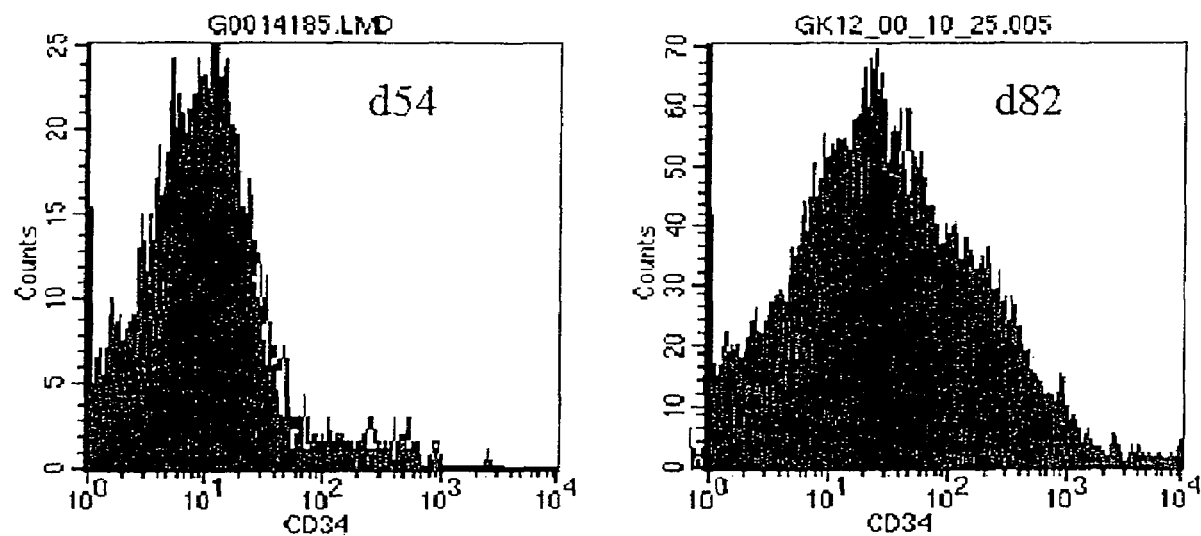
FIG. 6 shows a FACS kinetic for CD34 surface marker.

FIG. 6 shows a FACS kinetic for CD34 surface marker. The USSCs were grown in H5100/PEI for over 10 passages. During this culture period a significant increase of CD34 antigen expression was observed. With regard to the hematopoietic stem cell marker CD34, FIG. 6 reveals that in passage 3 until day 54 no CD34 positive cells can be detected. In contrast, in the seventh passage on day 82 a novel CD34 positive subpopulation is appearing. On the other hand, if such CD34 or/and FIK1 positive progenitors were cultured with cytokine conditioned medium specific for hematopoietic differentiation, the typical mixed or hematopoietic colonies for red and white blood cell precursors (CFU-GM and BFU-E) developed comparable to CD45+ hematopoeitic progenitor cells (Example 9).

Figure 7:
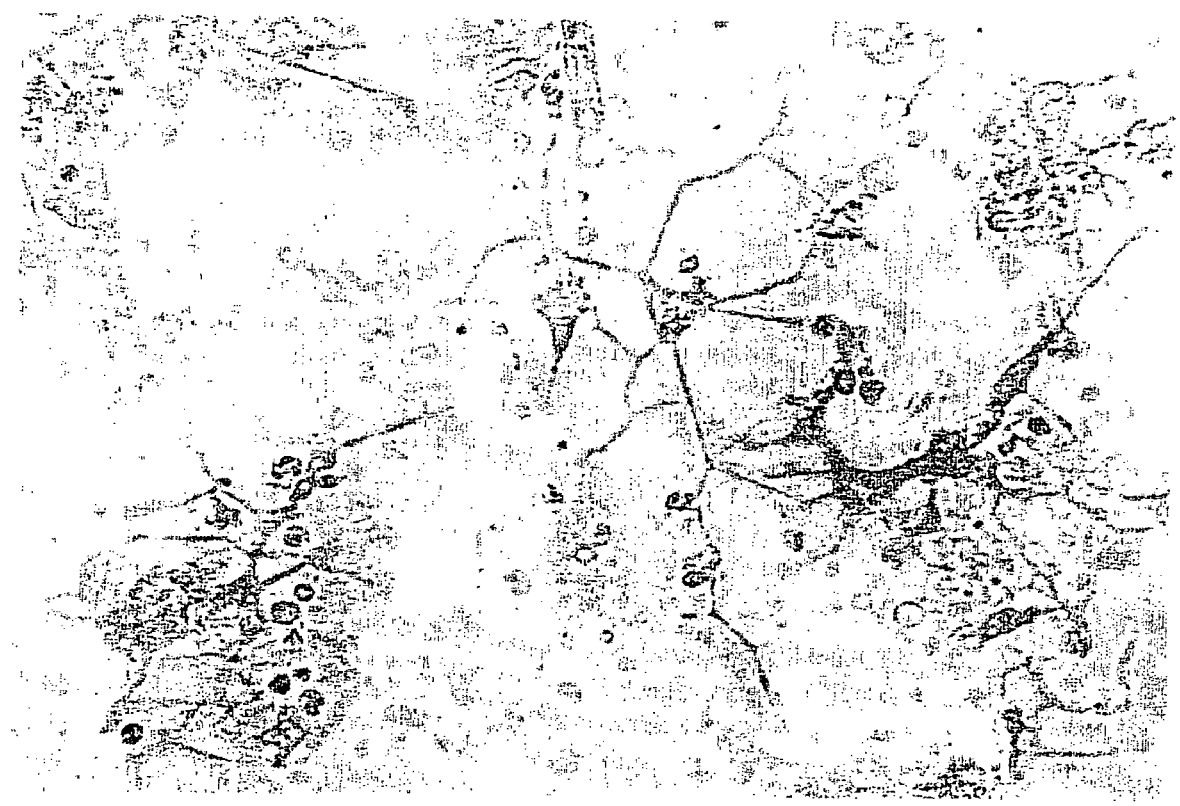
FIG. 7 shows a photomicrograph of USSC cells after neuronal induction.

On the other hand, if cord blood mononuclear cells depleted for CD14 are cultured in high glucose containing medium, they reveal the typical characteristics of neural stem cells. FIG. 7 shows a photomicrograph of USSC cells after neuronal induction. USSCs of the invention cultured in Dulbecco's modified eagle medium (DMEM) high glucose demonstrate an astrocyte-like morphology. FIG. 7 shows an example of such cultured cells showing glial morphology obtained after 13 days in culture (example 6). After being expanded with PEI, USSCs express the neural stem cell marker nestin. A first observation indicates that nestin staining is less pronounced after cells have been stimulated with neural inducing agents like retinoid acid (RA), basic fibroblast growth factor bFGF, and nerve growth factor β (NGF-β) (McKay, 1997).

Figure 8:
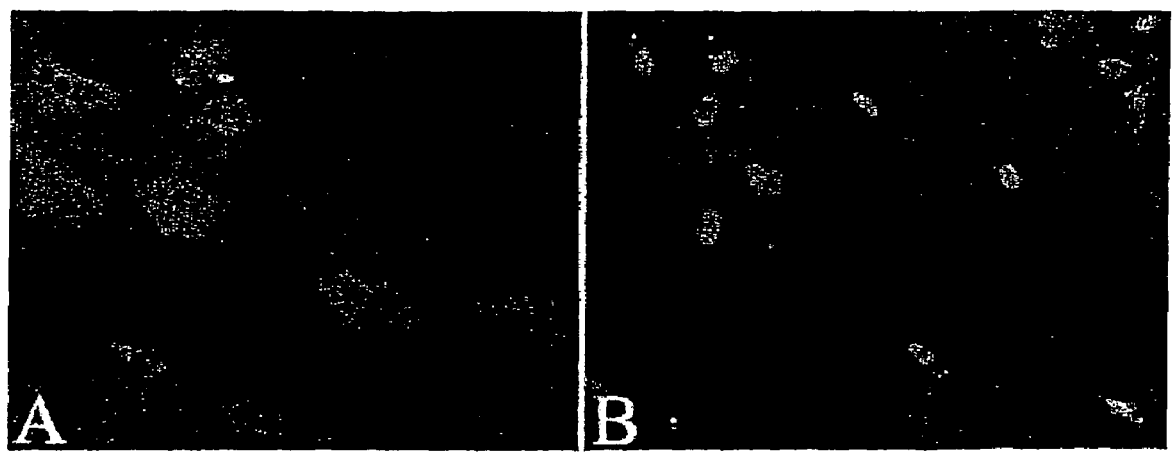
FIG. 8 shows that USSCs of the invention express the neural stem cell marker nestin anti-nestin immunostaining.

In detail, FIG. 8 shows USSCs of the invention expressing the neural stem cell marker nestin. (A) USSCs were incubated in H5100/PEI medium for 7 days and subjected to standard anti-nestin immunohistochemistry. (B) Cells were incubated for 7 days in H5100/PEI following 9 days of induction in H5100 with RA, bFGF, and NGF. Note that nestin staining is reduced compared to cells grown under conditions in (A).

Figure 9:
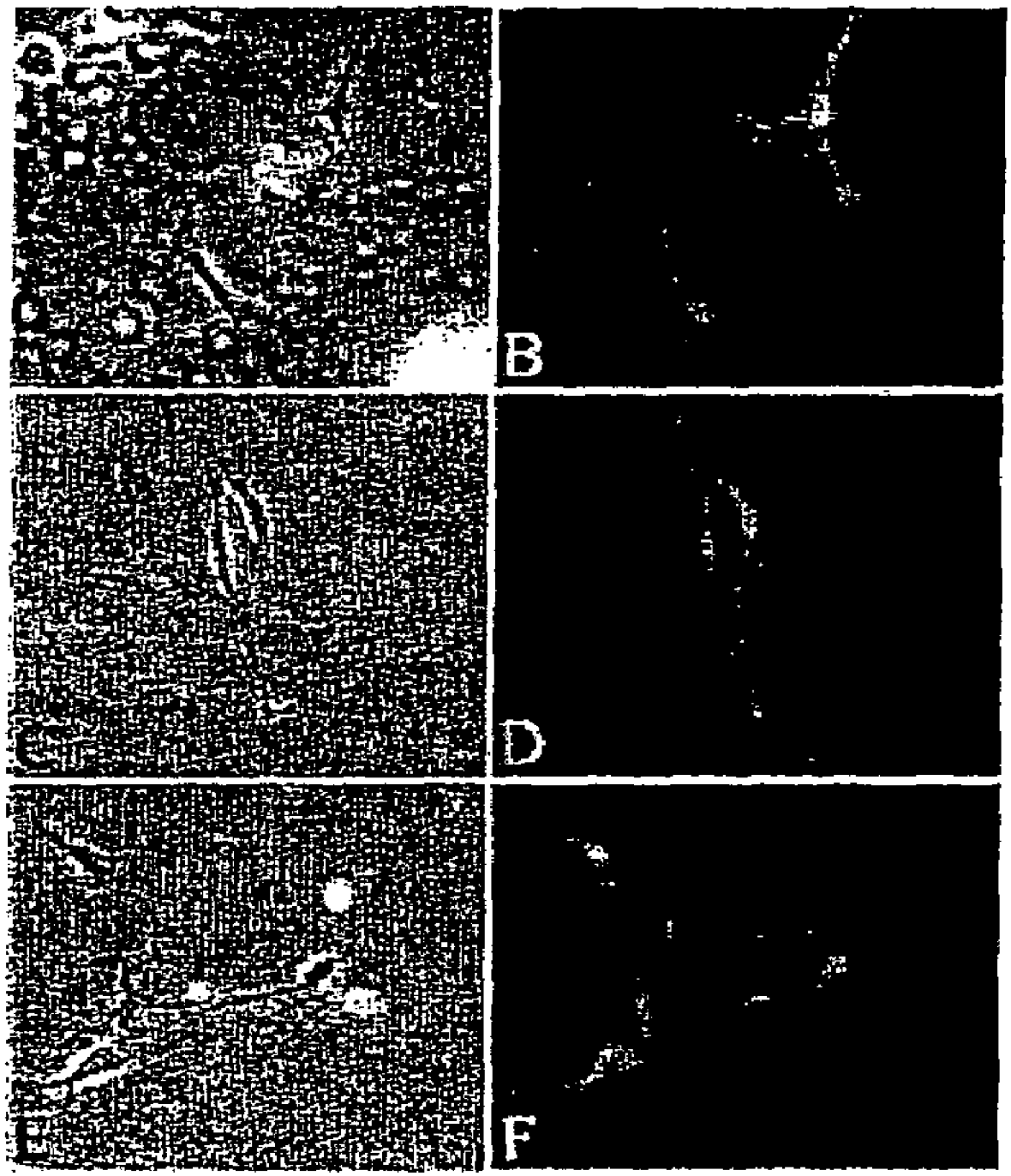
FIG. 9 shows USSCs generating cells of the neuronal lineage.
Figure 10:
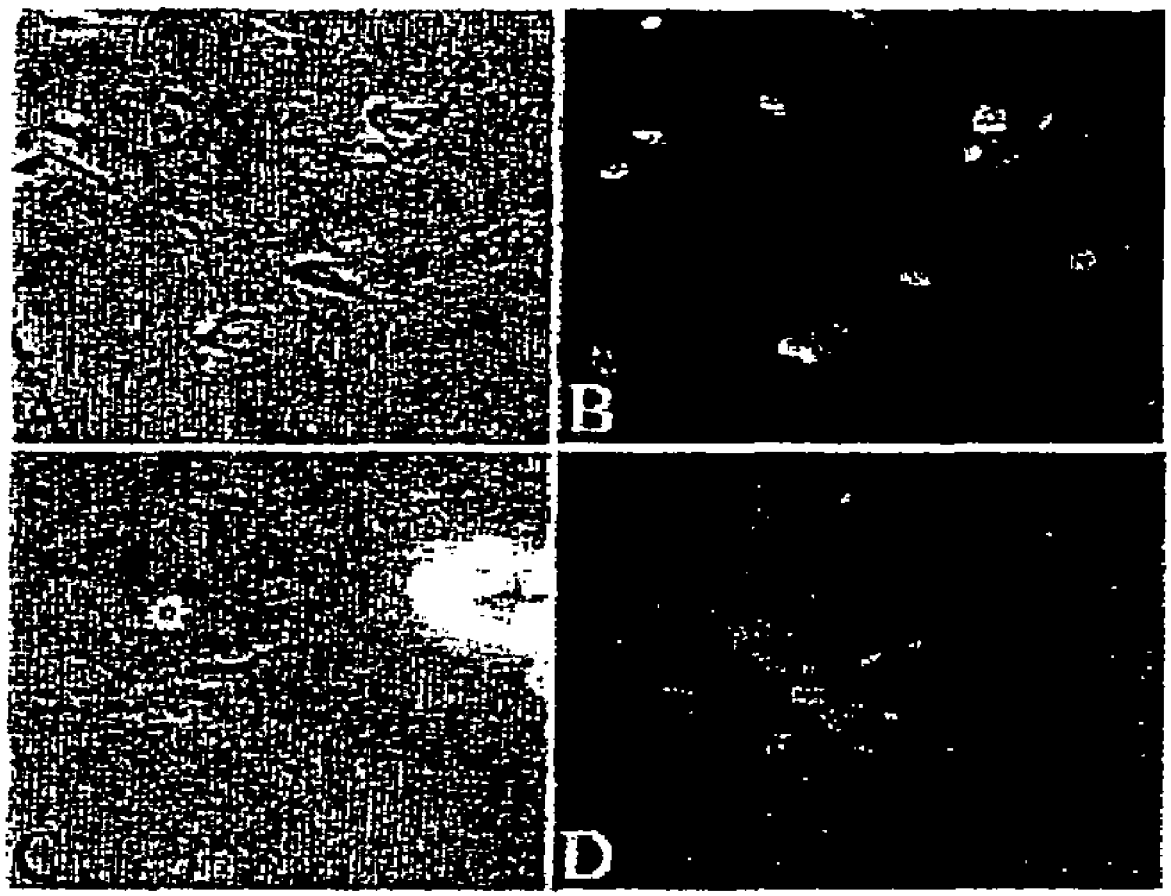
FIG. 10 shows USSCs generating cells of the glial lineage.

Further analysis of these cells reveals also expression of proteins characteristic for neural cells like γ-aminobutyric acid (GABA, FIG. 9B), tyrosine hydroxylase (FIG. 9B), synaptophysin (FIG. 9D), neurofilament (FIG. 9F), or typical glial antigens like galactocerebroside (GalC, FIG. 10B) and glial fibrillary acidic protein (GFAP, FIG. 10D). FIG. 9 shows USSCs of the invention generating cells of the neuronal lineage. USSCs of the invention were grown in H5100/PEI for 7 days and kept for 27 days on H5100 containing RA, bFGF and NGF. After standard fixation protocols, neuronal specific antibodies were applied. (A, C, D) Phase-contrast photographs, (B, D, F) fluorescence photographs of same preparations as in A, C, D. The DNA stainer DAPI (blue) is used to stain the nucleus of cells. (B) Double-immunofluorescence photograph using anti-GABA (red), and anti-tyrosine hydroxylase (TH, green). (D) An anti-synaptophysin staining (green). (F) A neuron specific anti-neurofilament staining is shown (red). A cocktail of antibodies against different subtypes of neurofilament was used. FIG. 10 shows USSCs of the invention generating cells of the glial lineage. Cells were subjected to the same cell culture conditions as shown in FIG. 9. DAPI is in blue. (A, C) Representation of phase contrast photographs. (B) Same cells as seen in (A) which have been subjected to anti-GalC immunostaining (red). (D) Same cell as in (C) stained with the anti-glial fibrillary acid protein (GFAP, red).

If, however, the above described universal stem cells are taken from any of the expansion passages and induced in DAG (dexamethasone, ascorbic acid, β-glycerol phosphate) containing culture conditions or in fibronectin containing medium, differentiation along the osteogenic lineage is induced (example 3). As shown in Table 2, bone specific marker genes (alkaline phosphatase, osteocalcin, collagen type I) are readily induced and detectable by RT-PCR.

TABLE 2

RT-PCR analysis during osteogenic differentiation of USSCs.

| | control | day 7 | day 14 |
|---|---|---|---|
| β-actin (pos. control) | + | + | + |
| alkaline phosphatase | − | + | + |
| collagen type II | − | + | + |
| osteocalcin | + | + | − |

All three marker genes of osteogenic differentiation show an increased mRNA expression at day 7 of DAG induction. β-actin serves as a positive control.

Figure 11A:
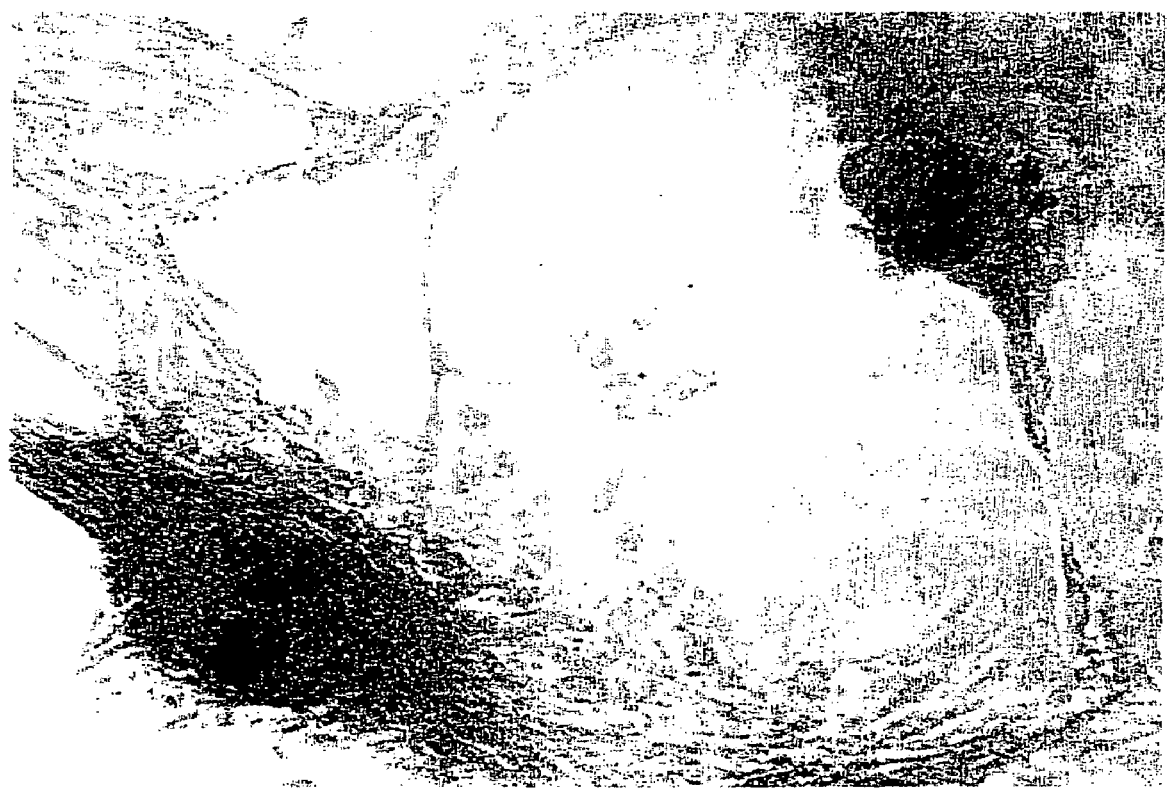
FIG. 11 shows mineralised nodule formation after osteogenic induction and after staining with alizarin red (B).
Figure 11B:
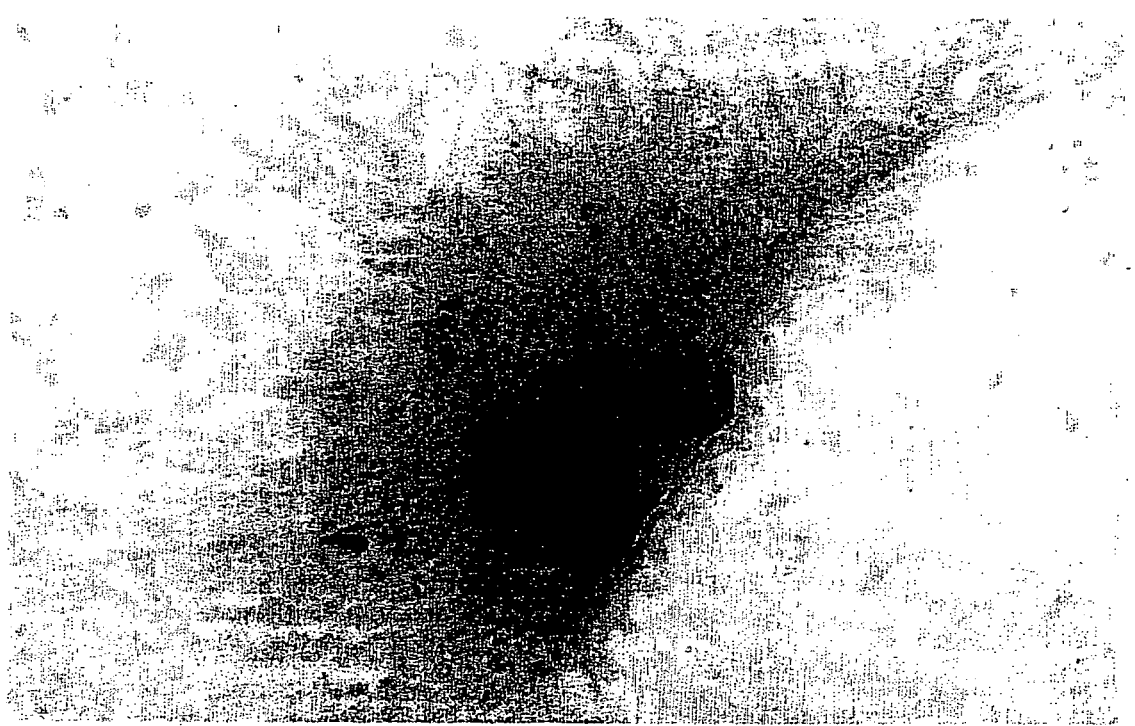

FIG. 11 shows a mineralised nodule formation after osteogenic induction and after staining with alizarin red (B). Osteogenic differentiation of nearly confluent USSC layers was induced by addition of dexamethasone, ascorbic acid and β-glycerolphosphate to the culture medium H5100. At day 10 of stimulation characteristic bone nodules appear (11A). Mineral deposition of these nodules can be demonstrated by Alizarin Red staining (11B). Under these osteogenic induction conditions, the cells of the invention undergo complete osteogenic differentiation as demonstrated by accumulation of mineralised bone in distinct nodules (FIG. 11A) which can be stained with Alizarin Red (FIG. 11B). Alternatively, the accumulation of hydroxyapatite in the cell culture can be detected after six days by von Kossa staining From these results it is evident, that cord blood contains a hitherto undetected very early stem cell which can be expanded to large quantities. In addition, this cell can be induced to differentiate into MSCs and from there into osteoblasts, as already demonstrated in FIG. 11A. After complete induction with DAG a further differentiation to mineralized bone nodules can be obtained, as shown in FIG. 11B with Alizarin Red staining.

The versatily of the cells of this invention is even greater as demonstrated by the chondrogenic differentiation after cultivation in DMEM high glucose containing dexamethasone, proline, sodium pyruvate, ITS+ Premix, and TGF-β1 (Johnstone et al., 1998). At day 0, and 14, of these differentiation experiments, cells were harvested and analyzed by RT-PCR (Table 3, example 4).

TABLE 3

RT-PCR analysis during chondrogenic differentiation of USSCs

|  | Control | day 14 |
|---|---|---|
| β-actin (pos. control) | + | + |
| Cart-1 | − | + |
| collagen type II (unspliced) | − | + |
| Chondroadherin | − | + |

At day 14 of chondrogenic stimulation three characteristic marker genes of on going chondrogenesis are expressed.

The results of these studies clearly demonstrate the upregulation of Cart-1, a specific chondrogenic transcription factor 14 days after chondrogenic stimulation. Furthermore mRNA transcripts for two typical cartilage extracellular proteins (collagen type II and chondroadherin) were also upregulated. Furthermore, the cells of this invention clearly produced extracellular proteoglycan molecules typical for chondrocytic differentiation as demonstrated by Alcian Blue staining. FIG. 12 shows Alcian Blue staining of USSC-derived pellet culture. USSCs were grown under sedimentation culture in a chondrogenic differentiation medium. After 6 days in induction medium, no significant amounts of proteoglycans (PG) as characteristic markers of chondrogenic differentiation are detectable by Alcian Blue staining (Panel A). In contrast, PGs are readily detectable as indicated by the blue/green color (Panel B).

Furthermore, the presence of the cartilage-specific collagen type II could be demonstrated at the protein level. FIG. 13: Collagen type II staining (green) of USSC cultures after chondrogenic differentiation.

USSCs were cultured in a chondrogenic differentiation medium. The expression of the extracellular matrix protein collagen type II at day 14 was demonstrated by fluorescence microscopy using anti-collagen type II primary antibody and a FITC anti-mouse secondary antibody (FIG. 13B).

The further versatility of the unrestricted stem cell is shown here by differentiation of such previously under the PEI-protocol expanded cultures into fat cells with higher concentrations of dexamethasone (example 5).

Figure 14:
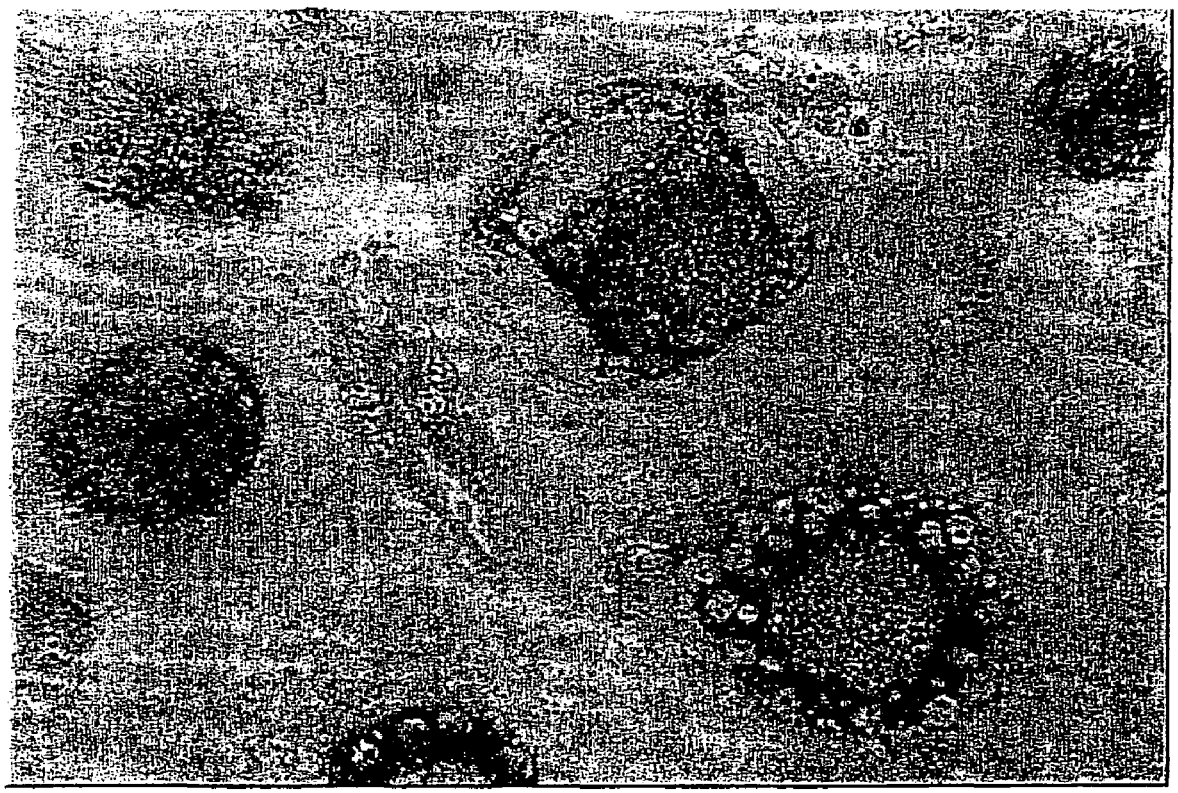
FIG. 14 shows adipogenic differentiation of USSC cultures as demonstrated by Oil Red staining.

FIG. 14 shows fat cells which can be specifically stained with Oil Red (Sigma). Adipocytes are characterized by a high amount of intracellular vesicles and a specific red staining with Oil Red.

Furthermore, USSCs when cultured for 24h in H5100 with 10μM 5'-azacytidine and subsequently with 100 ng/ml bFGF show strong evidence for muscle differentiation. A change in cell morphology is accompanied by the expression of slow-acting myosin (FIGS. 15 and 16).

Figure 17:
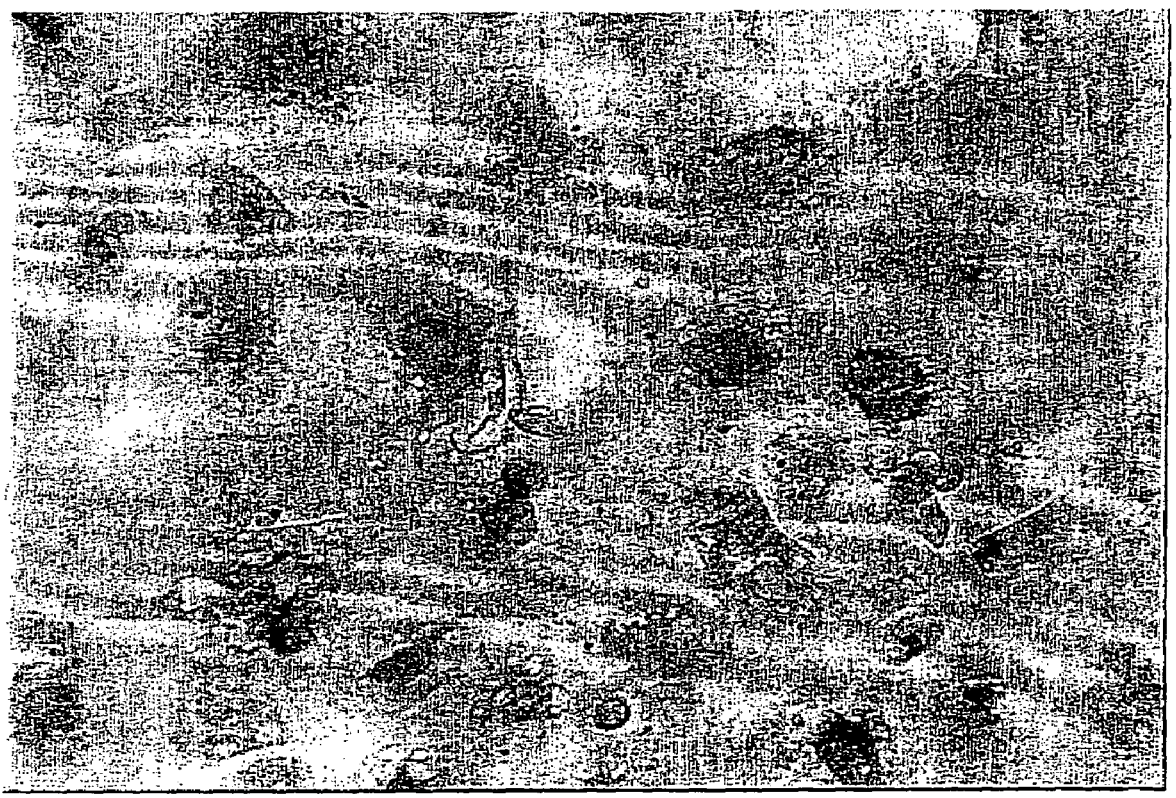
FIG. 17 shows oval cell phenotype of USSC derivatives.

In addition, the appearance and proliferation of typical oval cells is regularly observed in late passages (FIG. 17) when PEI induced USSCs are subcloned from the CD34+ subpopulation, which has been shown in FIG. 6 (example 8). These cells to variable degrees express the enzyme dipeptidyl peptidase IV, meaning that such oval cells can further differentiate into liver cells.

Figure 18:
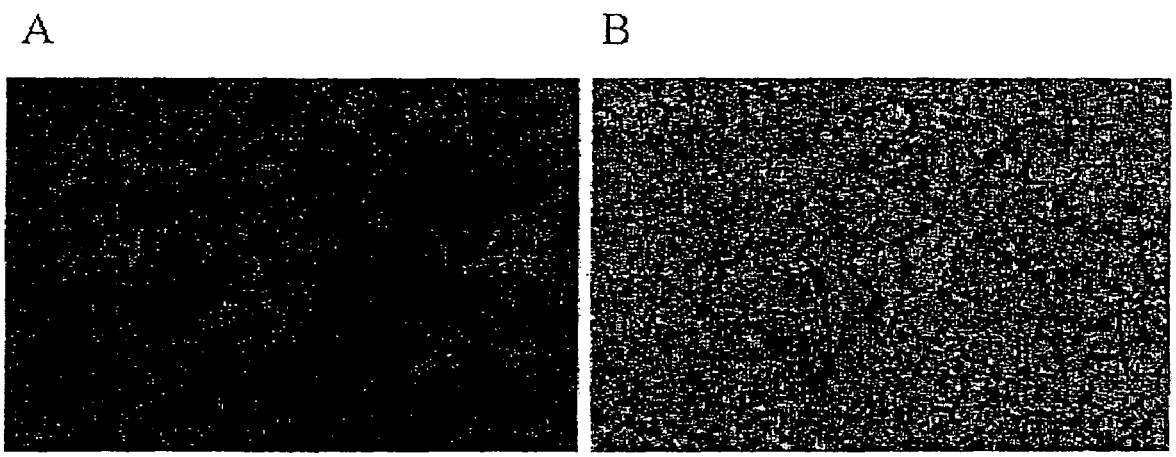
FIG. 18 shows survival and integration of USSC cultures after injection into SCID mouse liver parenchyma.

In vitro expanded USSC survive and persist after injection into regenerating livers of SCID mice with 50% partial hepatectomy as well as non-hepatectomised livers whereas cord blood derived mononuclear cells cannot be detected even when 25 fold higher cell numbers are transplanted. FIG. 18 shows the survival and integration of USSC cultures after injection into SCID mouse liver parenchyma. FIG. 18A: Red fluorescence 7 days after transplantation indicates survival and integration of human PKH26-labelled USSCs of the invention into the mouse liver tissue (without hepatectomy). In contrast, after transplantation of cord blood derived mononuclear cells (MNCs) no red fluorescence indicating integration of human MNCs was detectable. FIG. 18B: Cryo-section of mouse liver tissue corresponding to A: Transmission light micrograph of mouse liver tissue with integrated human USSCs.

Since the precursor for liver and pancreatic β island cells is identical, such CB-derived oval cells can also be differentiated into insulin producing β-island cells making them useful tools for cell therapy in diabetic patients or in patients with hepatic failure.

In addition to these obvious clinical applications any of the well characterized and under standardized conditions expanded stem cell components and their progeny can be used to monitor and define actions and molecular as well as cellular effects of newly developed pharmacological agents and thus substitute also for certain animal based experimentation.

Thus, these well standardized stem cells and differentiated cells derived from the human cord blood cultures described here be used as a valuable test reagent for the pharmaceutical and biomaterial industry.

USSC preparations under appropriate culture conditions developed multiple colonies of different hematopoietic lineages, providing evidence that these cells can give rise to hematopoiesis.

Under appropriately conditioned culture medium with defined concentrations of VEGF, Flt 3L, SCGF (stem cell growth factor) and in methyl-cellulose such cells develop mixed colonies with cells also positive for FLK1+ and AC133+, Tie1 and Tie2 markers. Upon further differentiation the marker profile characteristic for endothelial cells with AC133 negative, CD31+, CD54+, VWF+, VE-Catherin+ did develop.

The obvious utility of such endothelial cells for the in vitro growth of autologous and allogeneic blood vessels for therapy of vascular diseases is claimed here.

At the same time it is clear that all these in vitro generated and homogeneously expanded progenitors and their differentiated cells will—on a clonal level—serve as extremely important tools for the definition of the role of specific genes and their products in cell biology and all following medical applications based on cell- or molecule-mediated therapies.

Only small numbers of this unique cell type are sufficient to generate large numbers of adherently growing USSCs of the invention and the more differentiated mesenchymal stem cell for the production of medically applicable regenerative cell types.

One completely new aspect of this knowledge is the fact that such progenitors can asymmetrically develop into two or more distinctly differentiating cell types. This reveals a new biological principle of co-component regulation in functionally oriented cell regeneration taking place even in vitro.

The consequence of this invention is that stem cell based therapeutics have to be engineered according to this principle and not only consist of one clonal cell type. The invention is further described in the following non limiting examples.

EXAMPLE 1

Collection of Cord Blood (CB)

Collection of cord blood in the Obstetric Departments was performed with informed consent of the mother. After delivery of the baby with the placenta still in utero, the umbilical cord was doubly clamped and transsected 7-10 cm away from the umbilicus. After disinfection of the cord, the umbilical vein was punctured and CB collected into collection bags containing citrate phosphate dextrose (CPD) as anticoagulant.

Isolation of Mononuclear Cells from Cord Blood

Umbilical cord blood was carefully loaded onto Ficoll solution (density 1.077 g/cm$^3$). A density gradient centrifugation was performed (450 g, room temperature, 25 min). The mononuclear cells (MNC) of the interphase were collected and washed twice in phosphate buffer saline, pH 7,3 (PBS).

Generation of adherent layers of fibroblastoid morphology

Mononuclear cells were plated out at a density of about $5 \times 10^3$ cells/cm$^2$ in T25 culture flasks (Nunclon) [A.), B.), C.)]. Four different culture methods were used to initiate growth of adherent stem cells:
A.) CB-derived MNCs were initially cultured in Myelocult H5100 medium (StemCell Technologies, Vancouver/Canada) containing $10^{-7}$ M dexamethasone.
B.) CB-derived MNCs were initially cultured in Mesencult (StemCell Technologies, Vancouver/Canada) containing $10^{-7}$ M dexamethasone.
C.) B-derived MNCs were initially cultured in DMEM low glucose (Bio-Whittaker) with 30% FCS containing $10^{-7}$ M dexamethasone.
D.) CB-derived MNCs were plated at a density of $5 \times 10^6$/ml in 10 ml Myelocult H5100 Medium (StemCell Technologies, Vancouver, Canada) into 50 ml culture-flasks (Nunclon) without dexamethasone.

All cultures were incubated at 37° C. in 5% $CO_2$ in a fully humidified atmosphere, and were fed once a week by removing the complete medium with the non-adherent cells and adding 10 ml of fresh medium. After several time points the adherent spindle-shaped cells were removed by treatment with 0.050% trypsin and 0.53 mM EDTA for 2 min, rinsed with 50% serum-containing medium, collected by centrifugation at 780 g and analyzed by Flow cytometry or RT-PCR. After two to three weeks, adherent cells of fibroblastoid morphology appear in about 30% of all cell cultures.

Culture Condition for the Expansion of USSCs of the Invention

USSCs of the invention can be expanded in H5100 medium containing 10 ng/ml IGF I (Insulin-like growth factor-I), 10 ng/ml PDGF-BB (Platelet—derived growth factor-BB) and 10 ng/ml rh-human EGF (Recombinant Human epidermal growth factor) (PEI medium) at a density ranging from $1 \times 10^4$ and $1 \times 10^5$ cells/ml (expansion method A). Alternatively, USSC preparations can be expanded in the initial growth medium A, B, and C.

EXAMPLE 2

Immunophenotyping of Cells by Cytofluorometry

In order to determine the immunophenotype of USSCs, cells were stained with FITC-conjugated anti-CD45 (Becton Dickinson, Coulter), PE conjugated anti-CD14 (PharMingen, Coulter), anti-SSEA-4 (MC-813-70) labeled with goat F(ab')$_2$ anti-Mouse IgG+IgM (H+L)-FITC (Coulter), anti-CD10-PE (CALLA, PharMingen), anti-HLA-class I (, Coulter) labeled with goat F(ab')$_2$ anti-Mouse IgG+IgM (H+L)-FITC, anti-CD13-PE ( Becton Dickinson, Coulter); anti-CD29 (Coulter), anti CD44 (Coulter), anti-CD49e (Coulter), anti-CD90 (Coulter), anti-HLA-class II-FITC (Coulter). Cells were analyzed using an EPICS XL (Coulter) or a FACS analyzer (Becton Dickinson).

EXAMPLE 3

Demonstration of the Osteogenic Differentiation Potential of USSCs

USSCs obtained as described in example 1 were cultured in a standard medium until they reach 70% confluency. Osteogenic differentiation of these cells was induced by addition of $10^{-7}$ M dexamethasone, 50 µg/ml ascorbic acid, and 10 mM β-glycerolphosphat (Bruder et al. 1994, Jaiswal et al., 1997). At day 10 of stimulation, cells showed calcium phosphate deposits resulting in bone nodules. Mineralized bone nodules were detected by staining with Alizarin red as follows: The adherent cells in culture were washed twice with PBS, pH7.3 and stained with 5 ml 0.1% Alizarin Red solution for one hour at room temperature and subsequently with 0.1% acetic acid and absolute ethanol as well as PBS. Alizarin Red and von Kossa staining of calcium demonstrate the mineralisation potential of these cells (Stanford et al., 1995, Rungby et al., 1993). Osteogenic differentiation was also demonstrated by RT-PCR using the bone-specific differentiation markers osteocalcin (OC), osteopontin (OP), bone-specific alkaline phospatase (AP), bone sialo-protein (BSP), platelet-derived growth factor receptor alpha (PDGF-Ra), epidermal growth factor receptor (EGFR), and collagen type I.

EXAMPLE 4

Demonstration of the Chondrogenic Differentiation Potential of USSCs

For chondrogenic differentiation $2 \times 10^5$ adherent stem cells were placed in sedimentation culture in 15 ml polypropylen tubes. DMEM high glucose containing dexamethasone, proline, sodium pyruvate, ITS+ Premix, and TGF-β1 was used as cell culture medium (Johnstone et al., 1998, Yoo et al., 1998). At day 7, 14, and 21 cell fractions were analysed by RT-PCR for the cartilage specific gene products encoding Cart-1, collagen type II and chondroadherin. In addition, the USSCs were used in sedimentation cultures. After two weeks Dewax sections were fixed with 40% paraformaldehyde for 15 min at room temperature and washed in ethanol. Sections were stained in 1% Alcian Blue/3% acetic acid, pH 2,5 (Sigma) for 5 min and washed in distilled water. They clearly demonstrate a positive staining of specific proteoglycans as demonstrated by Alcian Blue staining (FIG. 12) (Chao, G. et al., 1993). After a chondrogenic induction period of 14 days cells were fixed according to a standard protocol and analyzed by fluorescense microscopy (Rosenbaum et al., 1998) demonstrating the presence of collagen type II specific extracellular matrix (FIG. 13B).

EXAMPLE 5

Demonstration of the Adipogenic Differentiation Potential of USSCs

USSC were cultured in H5100 containing $10^{-6}$ M dexamethasone, 50 µg/ml ascorbic acid and 10 mM β-glycerolphosphat resulting in partly differentiation of USSCs towards adipocytes as demonstrated by Oil Red staining (Ramirez-Zacarias et al., 1992).

EXAMPLE 6

Demonstration of the Neurogenic Differentiation Potential of USSCs

Cell isolation and culture conditions for glial cells

Mononuclear cord blood cells obtained as described were depleted for CD14+ cells by CD14/magnetic Activated Cell Sorting (MACS) isolation system employing VS+ separation columns according to the instructions of the manufacturer (Miltenyi Biotec, Bergisch Gladbach). The CD14 depleted mononuclear cells were cultured at a density of $2 \times 10^6$/ml in 10 ml High Glucose Medium (Dulbecco's MEM with 4500 G/L Glucose) into T25 culture-flasks (Nunclon) and incubated at 37° C. in 5% $CO_2$ in a fully humidified atmosphere. After 10-15 days in culture glial shaped cells were detected.

Differentiation Towards Neural Cells

A) Cells were expanded for 7 days either in H5100 medium alone or in the presence of 40 pg/ml PDGFB, 10 pg/ml EGF, 10 pg/ml IGF-I. Cells were trypsinized and plated at a density of about $3.5 \times 10^3$ cells /cm$^2$ in 24-well culture dishes on coverslips coated with poly D-lysin (PDL) and laminin (PDL/lam). Subsequently, neuronal differentiation was initiated by addition of inducing agents such as all-trans retinoid acid ($10^{-5}$ M), bFGF (20 ng/ml), and NGF-β (50 ng/ml).

Fluorescence Microscopy

After the induction period (27 days) cells were fixed according to a standard protocol (Rosenbaum et al., 1998) and stained with antibodies against neural specific antigens. Specimen were analyzed using fluorescence and transmission light microscopy.

EXAMPLE 7

Demonstration of Differentiation Potential in the Myocytic Lineage $1 \times 10^4$ USSCs were cultured in H5100 medium (StemCell Technology) supplemented with 10 ng/ml PDGFBB, 10 ng/ml EGF, 10 ng/ml IGF at 37° C., 5% $CO^2$ until they reach about 70% confluency. Thereafter cells were incubated with 10 µM 5'-azacytidine (Sigma) for 24 h, washed twice with PBS and cultured in H5100 medium supplemented with 100 ng/ml bFGF (Sigma). After 1 week in differentiation medium, the morphology of the cells changed (FIG. 15). After 10 days, the cells were trypsinized and transferred to fibronectin-coated glass chamber slide for immunostaining.

Immunohistochemistry

Cells were fixed with 5% formaldehyde/PBS for 15 min and washed twice in PBS, pH7.3. Using a standard protocol, cells were incubated with an anti-skeletal myosin (slow) specific primary antibody (clone NOQ7.5.4D, 1:400) (shown in green) and with anti-CD13 primary antibody (shown in red) or a monoclonal anti-skeletal myosin primary antibody (clone MY-32, 1:4000). Staining was positive for USSCs cultured under the above culture conditions (FIG. 16).

EXAMPLE 8

Human USSC cells as well as cord blood derived mononuclear cells (MNC) were labeled with the PKH26 RED Fluorescent Cell Linker Kit (Sigma, PKH26-GL). $2 \times 10^5$ USSCs and $5 \times 10^6$ MNCs were injected into the liver parenchyma of SCID mice with and without 50% hepatectomy. 7 days after transplantation complete liver regeneration was achieved for the hepatectomised animals. The liver tissue was analyzed by fluorescence microscopy of cryo-sections for the presence of red labelled human cells (FIG. 18).

EXAMPLE 9

Demonstration of the Differentiation Potential of USSC into the Hematopoietic Lineage Three different USSCs preperations (USSC$^{KCB55}$ in DMEM medium containing 30% FCS, USSC$^{KCB12}$ in H5100 medium containing dexamethasone, USSC$^{KCB13}$ in Mesen-Cult medium containing dexamethasone and USSC$^{GK12}$ in H5100 medium containing PEI) growing in appropriate expansion medium for extended periods (passage 5 to 8) were seeded in 250 µl ($2 \times 10^4$-$2 \times 10^5$ cells) of cell suspension in triplicate in 24-well plates in hematopoetic specific culture medium (Methocult 4434). Colonies of more than 50 cells were counted and classified as derived from granulocyte/macrophage (CFU-GM), early erythroid (BFU-E) or multipotent (CFU-GEMM) progenitor cells according to established criteria. Colony formation in different cultures was evident starting from 1 week of observation and followed up to 3 weeks under differentiation conditions. USSC preparations developed multiple colonies of different lineages, providing evidence that these cells can give rise to hematopoiesis.

EXAMPLE 10

Molecular Methods for the Analysis of Unrestricted Somatic Stem Cells and their Consecutive Differentiation Products PCR-primers for the amplification of specific cDNA sequences from osteocalcin, osteopontin, bone sialo-protein, alkaline phosphatase, PDGFRα and EGF receptor were selected from distinct respective exons, in order to be able to distinguish them in size of their respectively generated DNA fragments.

Via cloning into the pCRL1 vector (Invitrogen/USA) and consecutive transformation into E. coli strain TOP 10F the respective specific cDNA clones were obtained and characterized via cycle sequencing on an automated sequencer (Applied Biosystems).

RT-PCR reactions were performed in a two step procedure. 200 ng total RNA of the cells are first reverse transcribed with 10 U AMV Reverse Transcriptase (Promega, Mannheim), 1.5 pmol 3'-gene specific Primers, 1 mM dNTPs and the supplied buffer (Promega, Mannheim) in a volume of 20 µl for 1 h at 50° C. The PCR reaction was performed with 2 µl of the cDNA with 1 U HotStarTaq DNA Polymerase, buffer and Q-solution (Qiagen, Hilden), 1.5 mM dNTPs and 20 pmol 3'- and 5'-gene specific primer. The PCR reaction was carried out with a initiation step for 15 min at 95° C., 37 cycles at 94° C.

for 30 sec, 56° C. for 30 sec, 68° C. for 1 min and a final polymerization step for 5 min at 68° C.

TABLE 4

PCR-primers for the amplification of specific cDNA sequences
The table shows the 5'- and 3'- Primer sequences of the examined genes and the expected length of the PCR fragment in bp

| name | 5'primer sequence | | 3'primer sequence | | bp |
|---|---|---|---|---|---|
| PDGFR alpha | acagtggagattacgaatgtg | (SEQ ID NO: 1) | cacarcagtggtgatctcag | (SEQ ID NO: 2) | 251 |
| IGFR | cgagtggagaaatctgcgg | (SEQ ID NO: 3) | gaccagggcgtagttgtag | (SEQ ID NO: 4) | 272 |
| EGFR | tgccacaaccagtgtgct | (SEQ ID NO: 5) | ccacataattacggggacac | (SEQ ID NO: 6) | 205 |
| Neurofilament | attcgcgcgcagcttgaag | (SEQ ID NO: 7) | cctggtaggaggcaatgtc | (SEQ ID NO: 8) | 265 |
| GFAP | ctctccctggctcgaatgc | (SEQ ID NO: 9) | cctcctgataactggccg | (SEQ ID NO: 10) | 871 |
| Synaptophysin | cctgcagaacaagtaccgag | (SEQ ID NO: 11) | ccttgctgcccatagtcgc | (SEQ ID NO: 12) | 516 |
| Tyrosine hydroxylase | caccttcgcgcagttctcg | (SEQ ID NO: 13) | ctgtccagcacgtcgatgg | (SEQ ID NO: 14) | 387 |
| YB1 | ggtgaggaggcagcaaatgt | (SEQ ID NO: 15) | agggttggaatactgtggtc | (SEQ ID NO: 16) | 279 |
| Runx1 | gcaagctgaggagcggcg | (SEQ ID NO: 17) | gaccgacaaacctgaagtc | (SEQ ID NO: 18) | 296 |
| AML1c | cagtgcttcatgagagaatgc | (SEQ ID NO: 19) | gaccgacaaacctgaagtc | (SEQ ID NO: 20) | 453 |
| Cart-1 | ggagacgctggacaatgag | (SEQ ID NO: 21) | ggtagctgtcagtccttggc | (SEQ ID NO: 22) | 560 |
| CD105 | cctgccactggacacagg | (SEQ ID NO: 23) | atggcagctctgtggtgttg | (SEQ ID NO: 24) | 411 |
| Collagen Typ I | ggacacaatggattgcaagg | (SEQ ID NO: 25) | aaccactgctccactctgg | (SEQ ID NO: 26) | 441 |
| Collagen Typ II | tttcccaggtcaagatggtc | (SEQ ID NO: 27) | cttcagcacctgtctcacca | (SEQ ID NO: 28) | 377 |
| Osteocalcin | agtccagcaaaggtgcagc | (SEQ ID NO: 29) | ggccgtagaagcgccgat | (SEQ ID NO: 30) | 231 |
| alkaline phosphatase | gcttcagaagctcaacacca | (SEQ ID NO: 31) | cgttgtctgagtaccagtcc | (SEQ ID NO: 32) | 454 |
| beta actin | gagaaaatcttgcaccacac | (SEQ ID NO: 33) | ctcggtgaggatcttcat | (SEQ ID NO: 34) | 340 |

REFERENCES

Bruder S., Fink D J., and Caplan A I. (1994). Mesenchymal stem cells in bone formation, bone repair, and skeletal regeneration therapy. J. Cell. Biochem. 56: 284.

Caplan, A I., Mesenchymal stem cells. (1991) J. Orthop. Res. 9: 641-50.

Grompe, M and Finegold M. J. Liver Stem Cells./p. 455-497 from Stem Cell Biology, Cold Spring Harbor Laboratory Press, 2001.

Grompe, M. and Finegold M J. Liver stem cells. p. 455-497 from Stem Cell Biology, Cold Spring Harbor Laboratory Press, 2001.

Hall, C. L.; Yang, B.; Yang, X.; Zhang, S.; Turley, M.; Samuel, S.; Lange, L. A.; Wang, C.; Curpen, G. D.; Savani, R. C.; Greenberg, A. H.; Turley, E. A.:

Overexpression of the hyaluronan receptor RHAMM is transforming and is also required for H-ras transformation. Cell 82: 19-26, 1995.

Itano, N.; Kimata, K. Expression cloning and molecular characterization of HAS protein, a eukaryotic hyaluronan synthase. J. Biol. Chem. 271: 9875-9878, 1996

Jaiswal N, Haynesworth S E, Caplan A I, Bruder S P. Osteogenic differentiation of purified, culture-expanded human mesenchymal stem cells in vitro. J Cell Biochem. February 1997;64(2):295-312.

Johnstone B, Hering T M, Caplan A I, Goldberg V M, Yoo J U. In vitro chondrogenesis of bone marrow-derived mesenchymal progenitor cells. Exp Cell Res. Jan. 10, 1998;238 (1):265-72.

Knittel T, Kobold D, Piscaglia F, Saile B, Neubauer K, Mehde M, Timpl R, Ramadori G. Localization of liver myofibroblasts and hepatic stellate cells in normal and diseased rat livers: distinct roles of (myo-)fibroblast subpopulations in hepatic tissue repair. Histochem Cell Biol November 1999; 112(5):387-401

Kritzik M. R. and Sarvetnick N. Pancreatic Stem Cells, p. 499-513 from Stem Cell Biology, Cold Spring Harbor Laboratory Press, 2001.

Mareschi K, Biasin E, Piacibello W, Aglietta M, Madon E, Fagioli F. Haematologica October 2001;86(10):1099-100. Isolation of human mesenchymal stem cells: bone marrow versus umbilical cord blood.

Pan, T.-C.; Sasaki, T.; Zhang, R.-Z.; Fassler, R.; Timpl, R.; Chu, M.-L. : Structure and expression of fibulin-2, a novel extracellular matrix protein with multiple EGF-like repeats and consensus motifs for calcium binding. J. Cell Biol. 123: 1269-1277, 1993.

Ramirez-Zacarias J L, Castro-Munozledo F, Kuri-Harcuch W. Histochemistry July 1992;97(6):493-7. Quantitation of adipose conversion and triglycerides by staining intracytoplasmic lipids with Oil red O.

Rosenbaum, C., Kluwe, L., Mautner, V F., Friedrich, R. E., Müller, H W., Hanemann, C O. (1998): Enhanced proliferation and potassium conductance of Schwann cells isolated from NF2 schwannomas can be reduced by quinidine. Neurobiol Dis 5, 55-64.

Rungby J, Kassem M, Eriksen E F, Danscher G. Histochem J. June 1993;25(6):446-51. The von Kossa reaction for calcium deposits: silver lactate staining increases sensitivity and reduces background.

Stanford C M, Jacobson P A, Eanes E D, Lembke L A, Midura R J. J Biol Chem Apr. 21, 1995;270(16):9420-8. Rapidly forming apatitic mineral in an osteoblastic cell line (UMR 106-01 BSP).

Shapiro A. M. J., Lakey J. R. T., Ryan E. A., Korbutt G. S., Toth E., Warnock G. L., Kneteman N. M., Rajotte R. V. N Engl J Med Jul. 27, 2001; (343):230-238. Islet Transplantation in Seven Patients with Type 1 Diabetes Mellitus Using a Glucocorticoid-Free Immunosuppressive Regimen.

Sztrolovics, R.; Chen, X.-N.; Grover, J.; Roughley, P. J.; Korenberg, J. R.: Localization of the human fibromodulin gene (FMOD) to chromosome 1q32 and completion of the cDNA sequence. Genomics 23: 715-717, 1994.

Tsuda T, Wang H, Timpl R, Chu M L. Fibulin-2 expression marks transformed mesenchymal cells in developing cardiac valves, aortic arch vessels, and coronary vessels. Dev Dyn September 2001;222(1):89-100

Van der Schoot, C. E.; Huizinga, T. W. J.; Gadd, S. K.; Majdic, O.; Wijmans, R.; Knapp, W.; Von dem Borne, A. E. G.: Identification of three novel PI-linked proteins on granulocytes.In: Knapp, W.; Dorken, B.; Gilks, W. R.; Rieber, E. P.; Schmidt, R. E.; Stein, H.; Von dem Borne, A. E. G. K.: Leukocyte Typing IV: White Cell Differentiation Antigens. Oxford: Oxford Univ. Press (pub.) 1989. Pp. 887-891

Yoo J U, Barthel T S, Nishimura K, Solchaga L, Caplan A I, Goldberg V M, Johnstone B. The chondrogenic potential of human bone-marrow-derived mesenchymal progenitor cells. J. Bone Joint Surg Am. December 1998;80(12)-: 1745-57.

Zhang, R.-Z.; Pan, T.-C.; Zhang, Z.-Y.; Mattei, M.-G.; Timpl, R.; Chu, M.-L. Fibulin-2 (FBLN2): human cDNA sequence, mRNA expression, and mapping of the gene on human and mouse chromosomes. Genomics 22: 425-430, 1994.

Abbreviations

DAG osteogenic differentiation medium containing dexamethasone, ascorbic acid, and β-glycerolphosphat
HLA human leukocyte antigen
MSC mesenchymal stem cell
PEI medium containing PDGF-BB, EGF and IGF
SSEA4 stage-specific early antigen 4
USSC unrestricted somatic stem cell
PG proteoglycans

The invention claimed is:

1. A method for treating a cardiac muscle disease in a human patient in need of treatment for cardiac muscle disease, said method comprising administering to said patient isolated human unrestricted somatic stem cells (USSCs) from umbilical cord blood, wherein said USSCs are negative for the CD14 and CD45 antigens and positive for the CD13, CD29, CD44 and CD49e antigens, and wherein said USSCs express fibulin-2 and lack expression of hyaluronan synthase and fibromodulin, whereby said USSCs regenerate cardiac muscle cells in the heart of said patient and thereby treating said disease.

* * * * *

UNITED STATES PATENT AND TRADEMARK OFFICE
CERTIFICATE OF CORRECTION

| | | |
|---|---|---|
| PATENT NO. | : 7,556,801 B2 | Page 1 of 1 |
| APPLICATION NO. | : 10/758644 | |
| DATED | : July 7, 2009 | |
| INVENTOR(S) | : Wernet | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 570 days Delete the phrase "by 570 days" and insert -- by 595 days --

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,556,801 B2
APPLICATION NO. : 10/758644
DATED : July 7, 2009
INVENTOR(S) : Peter Wernet It is certified that error appears in the above-identified patent and that said Letters Patent is hereby corrected as shown below:

Title Page, in item (57) Abstract, replace "endothel" with --endothelial--.

Title Page 2, item (56) under OTHER PUBLICATIONS, in Shapiro et al., replace "glucocoriticoid-free" with --glucocorticoid-free--;

In Wernel et al., replace "Wernel et al.," with --Wernet et al.,--;

In Yoo et al., replace "chonddrogenic" with --chondrogenic--.

In the Specifications:

Column 2, Line 51, replace "can not" with --cannot--.

Column 3, Line 35, replace "neuropithelium" with --neuroepithelium--;

Line 44, replace "an other" with --another--.

Column 4, Line 66, replace "EngI" with --Engl--.

Column 5, Line 51, replace "FIK1" with --FlK1--;

Line 55, replace "hematopoeitic" with --hematopoietic--.

Column 7, Line 6, replace "staining" with --staining.--;

Line 15, replace "versatily" with --versatility--;

Line 34, replace "on going" with --ongoing--.

Signed and Sealed this
Thirtieth Day of April, 2013

Teresa Stanek Rea
*Acting Director of the United States Patent and Trademark Office*

CERTIFICATE OF CORRECTION (continued)
U.S. Pat. No. 7,556,801 B2

Column 9, Line 20, replace "transsected" with --transected--;

Line 55, replace "0.050%" with --0.05%--.

Column 10, Line 30, replace "β-glycerolphosphat" with --β-glycerophosphate--;

Line 34, replace "phospatase" with --phosphatase--;

Line 61, replace "40%" with --4%--.

Column 11, Lines 11-12, replace "β-glycerolphosphat" with --β-glycerophosphate--.

Column 12, Line 24, replace "preperations" with --preparations--;

Line 31, replace "hematopoetic" with --hematopoietic--.

Column 16, Line 24, replace "β-glycerolphosphat" with --β-glycerophosphate--.

SEQUENCE LISTING

```
<160> NUMBER OF SEQ ID NOS: 34

<210> SEQ ID NO 1
<211> LENGTH: 21
<212> TYPE: DNA
<213> ORGANISM: Artificial Sequence
<220> FEATURE:
<223> OTHER INFORMATION: Primer Sequence

<400> SEQUENCE: 1
acagtggaga ttacgaatgt g                                                21

<210> SEQ ID NO 2
<211> LENGTH: 20
<212> TYPE: DNA
<213> ORGANISM: Artificial Sequence
<220> FEATURE:
<223> OTHER INFORMATION: Primer Sequence

<400> SEQUENCE: 2
cacarcagtg gtgatctcag                                                  20

<210> SEQ ID NO 3
<211> LENGTH: 19
<212> TYPE: DNA
<213> ORGANISM: Artificial Sequence
<220> FEATURE:
<223> OTHER INFORMATION: Primer Sequence

<400> SEQUENCE: 3
cgagtggaga aatctgcgg                                                   19
```

<210> SEQ ID NO 4
<211> LENGTH: 19
<212> TYPE: DNA
<213> ORGANISM: Artificial Sequence
<220> FEATURE:
<223> OTHER INFORMATION: Primer Sequence

<400> SEQUENCE: 4
gaccagggcg tagttgtag                                                19

<210> SEQ ID NO 5
<211> LENGTH: 18
<212> TYPE: DNA
<213> ORGANISM: Artificial Sequence
<220> FEATURE:
<223> OTHER INFORMATION: Primer Sequence

<400> SEQUENCE: 5
tgccacaacc agtgtgct                                                 18

<210> SEQ ID NO 6
<211> LENGTH: 20
<212> TYPE: DNA
<213> ORGANISM: Artificial Sequence
<220> FEATURE:
<223> OTHER INFORMATION: Primer Sequence

<400> SEQUENCE: 6
ccacataatt acggggacac                                               20

<210> SEQ ID NO 7
<211> LENGTH: 19
<212> TYPE: DNA
<213> ORGANISM: Artificial Sequence
<220> FEATURE:
<223> OTHER INFORMATION: Primer Sequence

<400> SEQUENCE: 7
attcgcgcgc agcttgaag                                                19

<210> SEQ ID NO 8
<211> LENGTH: 19
<212> TYPE: DNA
<213> ORGANISM: Artificial Sequence
<220> FEATURE:
<223> OTHER INFORMATION: Primer Sequence

<400> SEQUENCE: 8
cctggtagga ggcaatgtc                                                19

<210> SEQ ID NO 9
<211> LENGTH: 19
<212> TYPE: DNA
<213> ORGANISM: Artificial Sequence
<220> FEATURE:
<223> OTHER INFORMATION: Primer Sequence

<400> SEQUENCE: 9
ctctccctgg ctcgaatgc                                                19

<210> SEQ ID NO 10
<211> LENGTH: 18
<212> TYPE: DNA
<213> ORGANISM: Artificial Sequence
<220> FEATURE:
<223> OTHER INFORMATION: Primer Sequence

```
<400> SEQUENCE: 10
cctcctgata actggccg                                                   18

<210> SEQ ID NO 11
<211> LENGTH: 20
<212> TYPE: DNA
<213> ORGANISM: Artificial Sequence
<220> FEATURE:
<223> OTHER INFORMATION: Primer Sequence

<400> SEQUENCE: 11
cctgcagaac aagtaccgag                                                 20

<210> SEQ ID NO 12
<211> LENGTH: 19
<212> TYPE: DNA
<213> ORGANISM: Artificial Sequence
<220> FEATURE:
<223> OTHER INFORMATION: Primer Sequence

<400> SEQUENCE: 12
ccttgctgcc catagtcgc                                                  19

<210> SEQ ID NO 13
<211> LENGTH: 19
<212> TYPE: DNA
<213> ORGANISM: Artificial Sequence
<220> FEATURE:
<223> OTHER INFORMATION: Primer Sequence

<400> SEQUENCE: 13
caccttcgcg cagttctcg                                                  19

<210> SEQ ID NO 14
<211> LENGTH: 19
<212> TYPE: DNA
<213> ORGANISM: Artificial Sequence
<220> FEATURE:
<223> OTHER INFORMATION: Primer Sequence

<400> SEQUENCE: 14
ctgtccagca cgtcgatgg                                                  19

<210> SEQ ID NO 15
<211> LENGTH: 20
<212> TYPE: DNA
<213> ORGANISM: Artificial Sequence
<220> FEATURE:
<223> OTHER INFORMATION: Primer Sequence

<400> SEQUENCE: 15
ggtgaggagg cagcaaatgt                                                 20

<210> SEQ ID NO 16
<211> LENGTH: 20
<212> TYPE: DNA
<213> ORGANISM: Artificial Sequence
<220> FEATURE:
<223> OTHER INFORMATION: Primer Sequence

<400> SEQUENCE: 16
agggttggaa tactgtggtc                                                 20

<210> SEQ ID NO 17
```

-continued

```
<211> LENGTH: 18
<212> TYPE: DNA
<213> ORGANISM: Artificial Sequence
<220> FEATURE:
<223> OTHER INFORMATION: Primer Sequence

<400> SEQUENCE: 17
gcaagctgag gagcggcg                                                 18

<210> SEQ ID NO 18
<211> LENGTH: 19
<212> TYPE: DNA
<213> ORGANISM: Artificial Sequence
<220> FEATURE:
<223> OTHER INFORMATION: Primer Sequence

<400> SEQUENCE: 18
gaccgacaaa cctgaagtc                                                19

<210> SEQ ID NO 19
<211> LENGTH: 21
<212> TYPE: DNA
<213> ORGANISM: Artificial Sequence
<220> FEATURE:
<223> OTHER INFORMATION: Primer Sequence

<400> SEQUENCE: 19
cagtgcttca tgagagaatg c                                             21

<210> SEQ ID NO 20
<211> LENGTH: 19
<212> TYPE: DNA
<213> ORGANISM: Artificial Sequence
<220> FEATURE:
<223> OTHER INFORMATION: Primer Sequence

<400> SEQUENCE: 20
gaccgacaaa cctgaagtc                                                19

<210> SEQ ID NO 21
<211> LENGTH: 19
<212> TYPE: DNA
<213> ORGANISM: Artificial Sequence
<220> FEATURE:
<223> OTHER INFORMATION: Primer Sequence

<400> SEQUENCE: 21
ggagacgctg gacaatgag                                                19

<210> SEQ ID NO 22
<211> LENGTH: 20
<212> TYPE: DNA
<213> ORGANISM: Artificial Sequence
<220> FEATURE:
<223> OTHER INFORMATION: Primer Sequence

<400> SEQUENCE: 22
ggtagctgtc agtccttggc                                               20

<210> SEQ ID NO 23
<211> LENGTH: 18
<212> TYPE: DNA
<213> ORGANISM: Artificial Sequence
<220> FEATURE:
<223> OTHER INFORMATION: Primer Sequence

<400> SEQUENCE: 23
```

-continued

| | |
|---|---|
| cctgccactg gacacagg | 18 |

<210> SEQ ID NO 24
<211> LENGTH: 20
<212> TYPE: DNA
<213> ORGANISM: Artificial Sequence
<220> FEATURE:
<223> OTHER INFORMATION: Primer Sequence

<400> SEQUENCE: 24

| | |
|---|---|
| atggcagctc tgtggtgttg | 20 |

<210> SEQ ID NO 25
<211> LENGTH: 20
<212> TYPE: DNA
<213> ORGANISM: Artificial Sequence
<220> FEATURE:
<223> OTHER INFORMATION: Primer Sequence

<400> SEQUENCE: 25

| | |
|---|---|
| ggacacaatg gattgcaagg | 20 |

<210> SEQ ID NO 26
<211> LENGTH: 19
<212> TYPE: DNA
<213> ORGANISM: Artificial Sequence
<220> FEATURE:
<223> OTHER INFORMATION: Primer Sequence

<400> SEQUENCE: 26

| | |
|---|---|
| aaccactgct ccactctgg | 19 |

<210> SEQ ID NO 27
<211> LENGTH: 20
<212> TYPE: DNA
<213> ORGANISM: Artificial Sequence
<220> FEATURE:
<223> OTHER INFORMATION: Primer Sequence

<400> SEQUENCE: 27

| | |
|---|---|
| tttcccaggt caagatggtc | 20 |

<210> SEQ ID NO 28
<211> LENGTH: 20
<212> TYPE: DNA
<213> ORGANISM: Artificial Sequence
<220> FEATURE:
<223> OTHER INFORMATION: Primer Sequence

<400> SEQUENCE: 28

| | |
|---|---|
| cttcagcacc tgtctcacca | 20 |

<210> SEQ ID NO 29
<211> LENGTH: 19
<212> TYPE: DNA
<213> ORGANISM: Artificial Sequence
<220> FEATURE:
<223> OTHER INFORMATION: Primer Sequence

<400> SEQUENCE: 29

| | |
|---|---|
| agtccagcaa aggtgcagc | 19 |

<210> SEQ ID NO 30
<211> LENGTH: 18
<212> TYPE: DNA

```
<213> ORGANISM: Artificial Sequence
<220> FEATURE:
<223> OTHER INFORMATION: Primer Sequence

<400> SEQUENCE: 30
ggccgtagaa gcgccgat                                                18

<210> SEQ ID NO 31
<211> LENGTH: 20
<212> TYPE: DNA
<213> ORGANISM: Artificial Sequence
<220> FEATURE:
<223> OTHER INFORMATION: Primer Sequence

<400> SEQUENCE: 31
gcttcagaag ctcaacacca                                              20

<210> SEQ ID NO 32
<211> LENGTH: 20
<212> TYPE: DNA
<213> ORGANISM: Artificial Sequence
<220> FEATURE:
<223> OTHER INFORMATION: Primer Sequence

<400> SEQUENCE: 32
cgttgtctga gtaccagtcc                                              20

<210> SEQ ID NO 33
<211> LENGTH: 20
<212> TYPE: DNA
<213> ORGANISM: Artificial Sequence
<220> FEATURE:
<223> OTHER INFORMATION: Primer Sequence

<400> SEQUENCE: 33
gagaaaatct tgcaccacac                                              20

<210> SEQ ID NO 34
<211> LENGTH: 18
<212> TYPE: DNA
<213> ORGANISM: Artificial Sequence
<220> FEATURE:
<223> OTHER INFORMATION: Primer Sequence

<400> SEQUENCE: 34
ctcggtgagg atcttcat                                                18
```